US011925216B2

(12) United States Patent
Bajpai et al.

(10) Patent No.: US 11,925,216 B2
(45) Date of Patent: Mar. 12, 2024

(54) SYSTEM AND METHOD FOR FILLING OF CARTRIDGES FOR PORTABLE VAPORIZING DEVICES

(71) Applicant: Puff Corporation, Los Angeles, CA (US)

(72) Inventors: Avinash Bajpai, Aguora Hills, CA (US); Roger Sayre, Los Angeles, CA (US); Charlton Huang, Irvine, CA (US); John Biondo, Los Angeles, CA (US); Ori Russo, Los Angeles, CA (US); Cyrus Legg, Los Angeles, CA (US)

(73) Assignee: Puff Corporation, Los Angeles, CA (US)

( * ) Notice: Subject to any disclaimer, the term of this patent is extended or adjusted under 35 U.S.C. 154(b) by 0 days.

(21) Appl. No.: 18/235,604

(22) Filed: Aug. 18, 2023

(65) Prior Publication Data
US 2023/0389618 A1   Dec. 7, 2023

Related U.S. Application Data

(63) Continuation of application No. PCT/US2023/015450, filed on Mar. 17, 2023.
(Continued)

(51) Int. Cl.
*A24F 40/42* (2020.01)
*A24F 40/485* (2020.01)
(Continued)

(52) U.S. Cl.
CPC .............. *A24F 40/70* (2020.01); *A24F 40/42* (2020.01); *A24F 40/485* (2020.01); *B65B 39/02* (2013.01);
(Continued)

(58) Field of Classification Search
CPC .......... A24F 42/80; A24F 40/70; A24F 40/42; A24F 40/485
See application file for complete search history.

(56) References Cited

U.S. PATENT DOCUMENTS

| 5,353,813 A | 10/1994 | Deevi |
| D492,061 S | 6/2004 | Reynolds |

(Continued)

FOREIGN PATENT DOCUMENTS

| WO | 2020065077 | 4/2020 |
| WO | 2020123931 | 6/2020 |

OTHER PUBLICATIONS

International Search Report and Written Opinion for PCT/US2023/015450 dated Jul. 11, 2023.
(Continued)

*Primary Examiner* — James Harvey
(74) *Attorney, Agent, or Firm* — Bryan Cave Leighton Paisner LLP

(57) ABSTRACT

A portable vaporizing device and/or cartridge comprises a product chamber capable of holding a vaporizable product therein, and a porous valve element configured to be heated to flow the vaporizable product therethrough and generate vapor from the vaporizable product, and optionally including a heat transfer element to heat the vaporizable product as it flows through the product chamber towards the porous valve element. Also provided are methods and automated systems for filling the cartridge used in the portable vaporizing device with a vaporizable product.

12 Claims, 33 Drawing Sheets

Related U.S. Application Data

(60) Provisional application No. 63/321,306, filed on Mar. 18, 2022.

(51) Int. Cl.
*A24F 40/70* (2020.01)
*B65B 39/02* (2006.01)
*B65B 39/12* (2006.01)
*B65B 63/08* (2006.01)
*A24F 42/80* (2020.01)

(52) U.S. Cl.
CPC ............. *B65B 39/12* (2013.01); *B65B 63/08* (2013.01); *A24F 42/80* (2020.01)

(56) References Cited

U.S. PATENT DOCUMENTS

| | | |
|---|---|---|
| D760,429 S | 6/2016 | Emarlou |
| 9,609,894 B2 | 4/2017 | Abramov et al. |
| 9,648,909 B2 | 5/2017 | Zhou et al. |
| 10,080,387 B2 | 9/2018 | Phillips et al. |
| 10,092,041 B1 | 10/2018 | Rinehart et al. |
| D833,064 S | 11/2018 | Verleur et al. |
| 10,117,461 B2 | 11/2018 | Chen |
| 10,130,122 B2 | 11/2018 | Anderson |
| 10,136,679 B1 | 11/2018 | Shotey et al. |
| 10,159,282 B2 | 12/2018 | Monsees et al. |
| D843,650 S | 3/2019 | Verleur et al. |
| D861,147 S | 9/2019 | He et al. |
| D864,746 S | 10/2019 | Franco |
| 11,129,417 B2 | 9/2021 | Volodarsky et al. |
| 2014/0109921 A1 | 4/2014 | Chen |
| 2015/0136124 A1 | 5/2015 | Aronie |
| 2016/0242465 A1 | 8/2016 | Zheng et al. |
| 2016/0295915 A1 | 10/2016 | Jochnowitz et al. |
| 2017/0121169 A1 | 5/2017 | Dailey et al. |
| 2017/0233114 A1 | 8/2017 | Christensen et al. |
| 2017/0238617 A1 | 8/2017 | Scatterday |
| 2017/0340011 A1 | 11/2017 | Batista |
| 2018/0029782 A1 | 2/2018 | Zuber |
| 2018/0064170 A1 | 3/2018 | Peuchert et al. |
| 2018/0110263 A1 | 4/2018 | Borkovec et al. |
| 2018/0132534 A1 | 5/2018 | Reevell |
| 2018/0132535 A1 | 5/2018 | Reevell |
| 2018/0160737 A1 | 6/2018 | Verleur et al. |
| 2018/0177240 A1 | 6/2018 | Duque et al. |
| 2018/0272083 A1 | 9/2018 | Avots |
| 2018/0289909 A1 | 10/2018 | Lindars et al. |
| 2019/0008206 A1 | 1/2019 | Gimkiewicz |
| 2019/0098933 A1 | 4/2019 | Courbat et al. |
| 2019/0166913 A1 | 6/2019 | Trzecieski |
| 2019/0373953 A1 | 12/2019 | Atkins et al. |
| 2020/0077709 A1* | 3/2020 | Volodarsky ............ A24F 40/485 |
| 2020/0077710 A1* | 3/2020 | Volodarsky ............ A61M 15/06 |
| 2020/0054077 A1 | 8/2020 | Chen |
| 2021/0045446 A1* | 2/2021 | Kuo ......................... D21J 3/00 |
| 2021/0127743 A1 | 5/2021 | Miller |
| 2021/0345679 A1 | 11/2021 | Volodarsky et al. |
| 2023/0172264 A1* | 6/2023 | Tesfatsion ............... A24F 40/20 131/328 |

OTHER PUBLICATIONS

Patent Cooperation Treaty, International Search Report for PCT/US2019/049858, 3 pages dated Nov. 4, 2019.
Vaporizer Chief, LLC, Pulsar APX Vape, retrieved from www.vaporizerchief.com/pulsar-apx-vape-vs/ 2020.
Patent Cooperation Treaty, International Search Report for PCT/US2023/015450, 3 pages, dated Jul. 11, 2023.

* cited by examiner

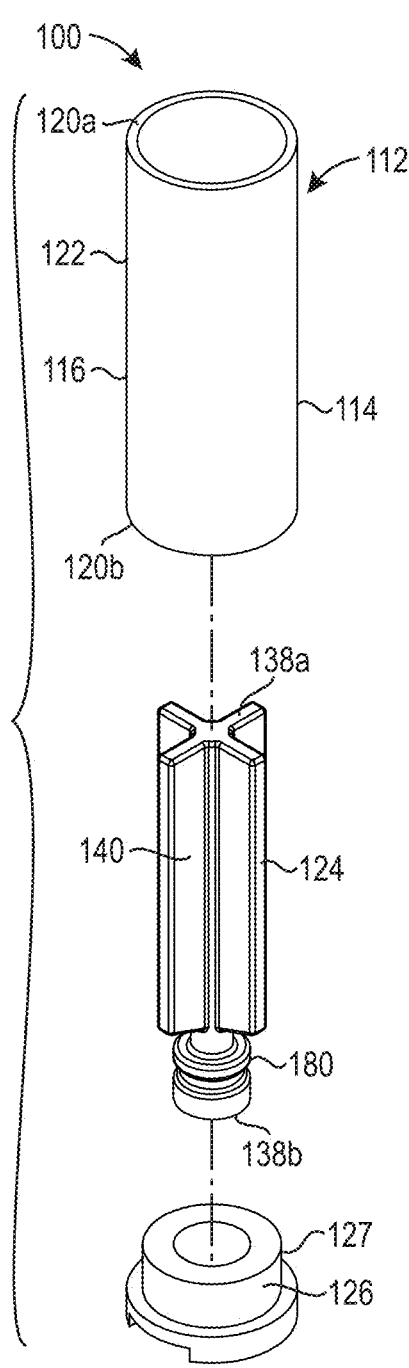
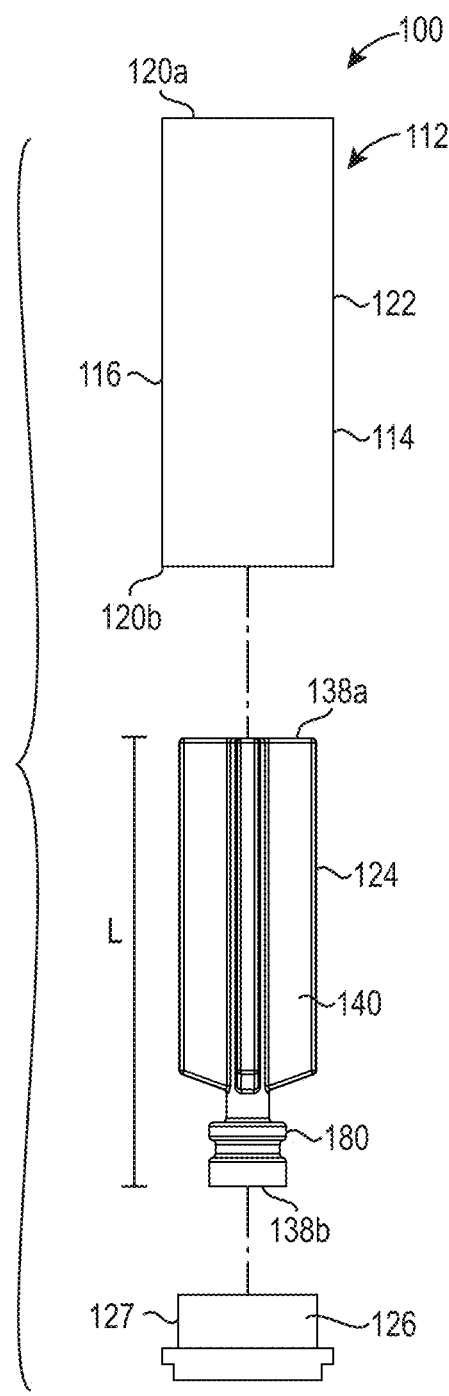
FIG. 1A
FIG. 1B

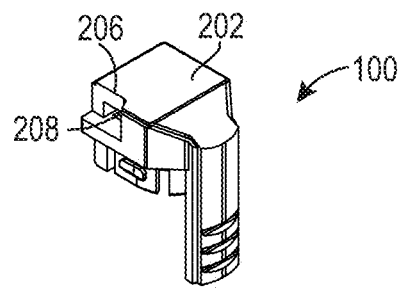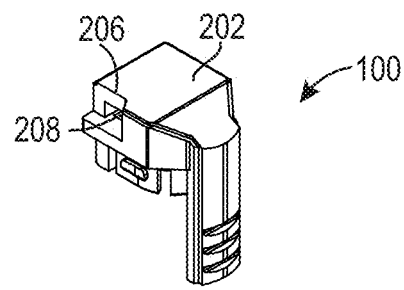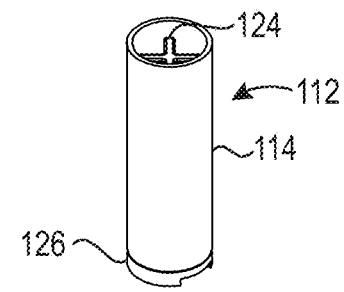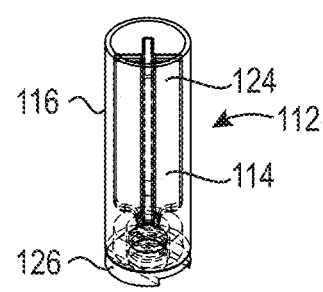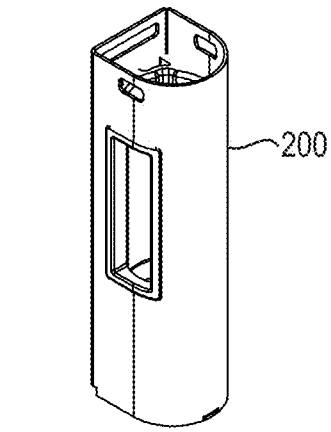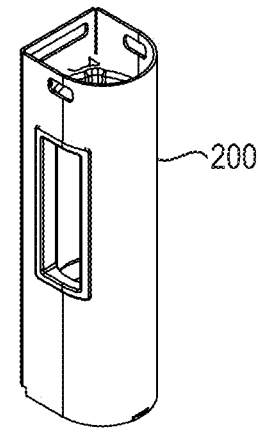
FIG. 14A                    FIG. 14B

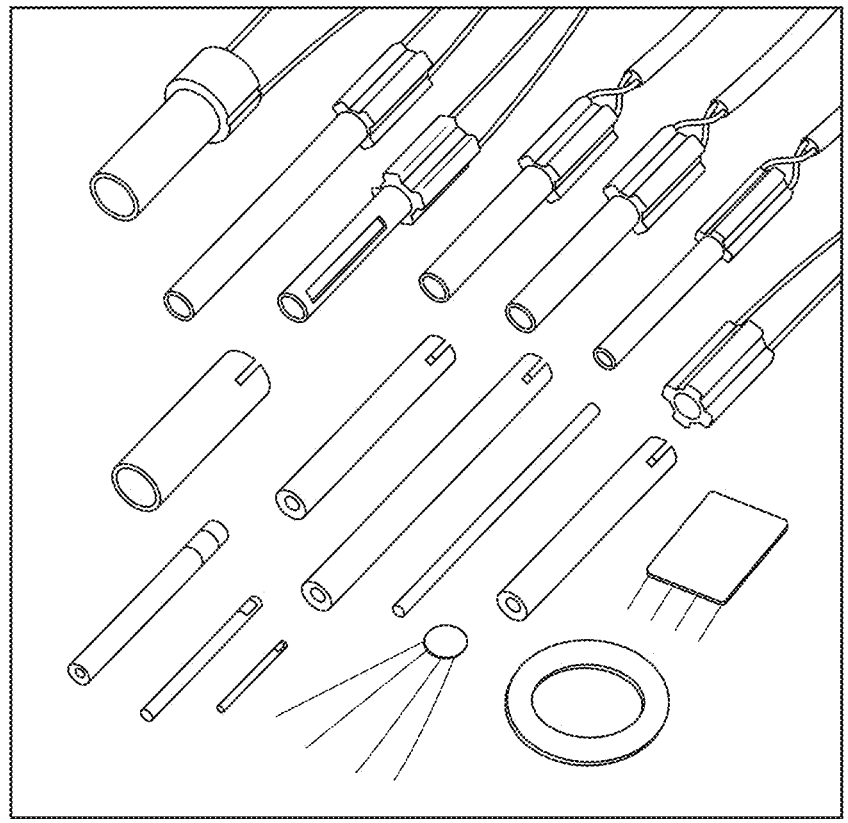
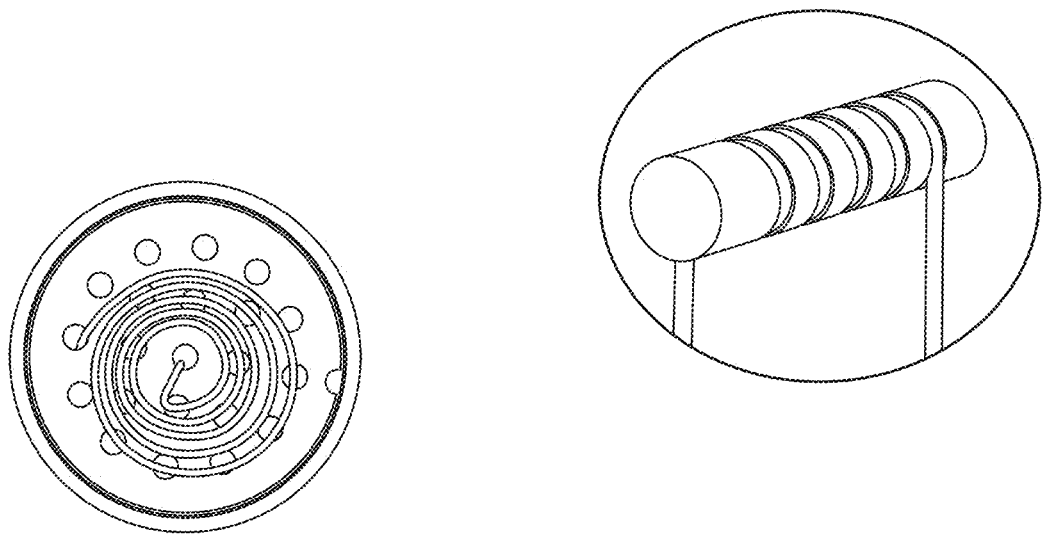
FIG. 17

SYSTEM AND METHOD FOR FILLING OF CARTRIDGES FOR PORTABLE VAPORIZING DEVICES

CROSS-REFERENCE TO RELATED APPLICATIONS

The present application is a continuation of International Application No. PCT/US2023/015450, filed Mar. 17, 2023, which claims priority to U.S. provisional application No. 63/321,306 filed on Mar. 18, 2022. The entire contents of the above applications are incorporated by reference as if recited in full herein.

FIELD OF THE INVENTION

Aspects of the present invention relate to methods and systems for filling of cartridges and/or portable vaporizing devices having such cartridges, with a vaporizable product.

BACKGROUND

Electronic portable vaporizers are used for aroma and/or inhalation therapy of vaporized oils such as cannabis, lavender, chamomile or any other plant material. More specifically, "pre-fill" vaporizers include cartridges containing a heating element and fibrous wick, usually cotton. By capillary action, which is the ability of a liquid to flow in narrow spaces without the assistance of external forces like gravity, the oil is moved from a wet area through the fibrous material to a dry area in which the oil can be vaporized by the heating element before inhalation. Vaporizers are regarded by the public as one of the easiest and healthiest ways to inhale cannabis; however the current technology used in pre-filled vaporizers results in a decrease in both quality of oil and in overall health benefit.

In the pre-fill vaporizer industry, a common problem that is encountered is that the cannabis product intended for inhalation is produced in a solid or semi-solid form, and/or may simply be too viscous to be moved through a wick via capillary action out of the wet chamber. One means of addressing this problem is to add substances that can thin the cannabis product, such as propylene glycol (PG), which is used as a thinning agent and/or diluent in a number of products. However, it is believed that such substances added to the cannabis product can have a deleterious effect on the lungs upon inhalation thereof, and thus are best avoided. A highly viscosity vaporizable product can also pose issues for filling or refilling of the vaporizer cartridge, as the viscous vaporizable product can be difficult to introduce into the cartridge in a reasonable manner.

Accordingly, there is a need for improved methods and systems for filling and/or refilling of portable vaporizing devices and cartridges used in such devices, with vaporizable product.

SUMMARY

According to one embodiment, a method for filling a cartridge used in a portable vaporizing device with a vaporizable product is provided. The cartridge comprises a vaporizable product receiving chamber configured to receive a vaporizable product therein and having upper and lower opposing ends, one or more internal heat-conducting surfaces within the vaporizable product receiving chamber and extending in between the upper and lower opposing ends thereof, and a porous valve element, the porous valve element being configured to at least partially vaporize the vaporizable product as it exits the vaporizable product receiving chamber by passing therethrough. The method comprises: heating the one or more internal heat-conducting surfaces; introducing the vaporizable product into the upper end of the vaporizable product receiving chamber, such that the vaporizable product flows along the heated one or more internal heat-conducting surfaces towards the lower end of the vaporizable product receiving chamber; and optionally, pre-heating the vaporizable product prior to introducing into the vaporizable product receiving chamber.

According to still another embodiment, an automated system for filling a cartridge used in a portable vaporizing device with a vaporizable product is provided. The cartridge comprises a vaporizable product receiving chamber configured to receive a vaporizable product therein and having upper and lower opposing ends, one or more internal heat-conducting surfaces within the vaporizable product receiving chamber and extending in between the upper and lower opposing ends thereof, and a porous valve element, the porous valve element being configured to at least partially vaporize the vaporizable product as it exits the vaporizable product receiving chamber by passing therethrough. The system comprises: a housing; a heating system configured to heat the one or more internal heat-conducting surfaces by supplying a power from a power source; a holder within the housing configured to hold the cartridge; an injection system within the housing configured to inject vaporizable product into the cartridge; and a controller configured to control the heating system and injection system; wherein the controller is configured to control the heating system to heat the one or more internal heat-conducting surfaces, and is configured to control the injection system to inject the vaporizable product into the upper end of the vaporizable product receiving chamber, such that the vaporizable product is at least partially melted and/or the viscosity of the vaporizable product is reduced as the vaporizable product flows along the heated one or more internal heat-conducting surfaces towards the lower end of the vaporizable product receiving chamber; and optionally wherein the heating system is configured to pre-heat the vaporizable product in the injection system prior to introducing into the vaporizable product receiving chamber.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1C are exploded views of an embodiment of a cartridge for a vaporizable product, according to aspects herein;

FIGS. 14A-14B are exploded views of a vaporizing device suitable for use with a cartridge according to aspects herein;

FIG. 17 depicts embodiments of heating elements suitable for use with a vaporizing device according to aspects herein;

DETAILED DESCRIPTION OF THE INVENTION

Figure 1C:
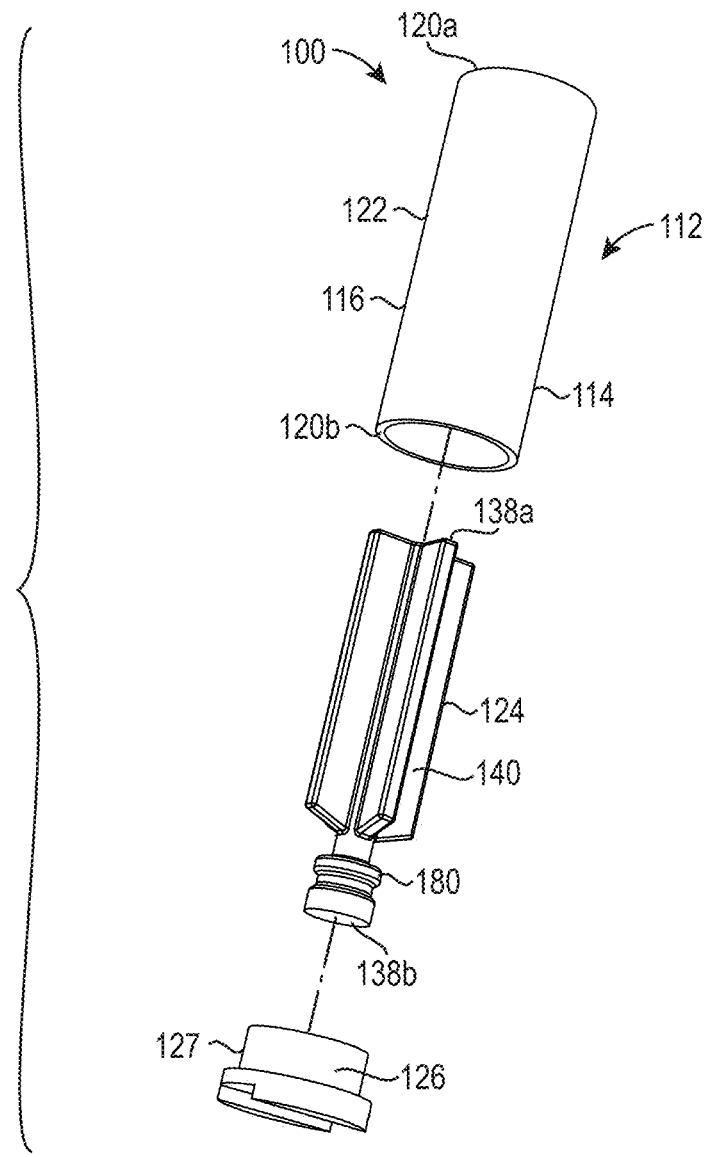
Figure 2A:
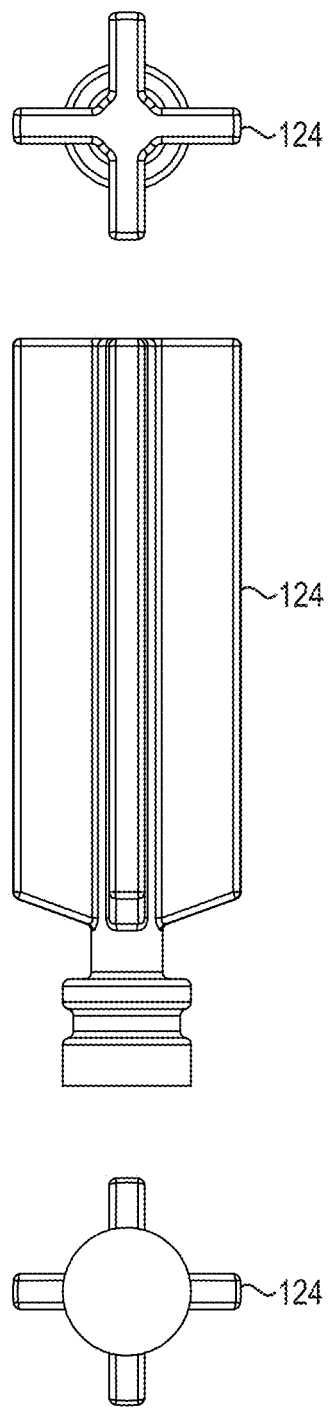
FIGS. 2A-2B are profile views of an embodiment of a heat transfer element according to aspects herein.
Figure 2B:
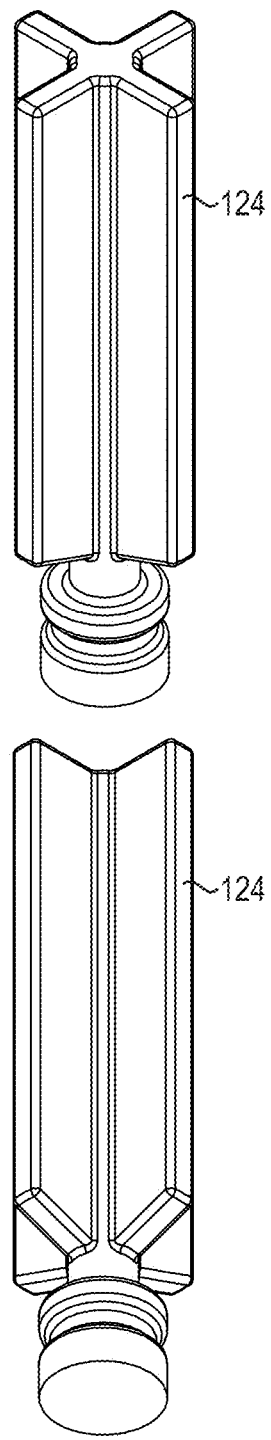

Aspects of the invention as described herein are directed to systems and methods for filling and/or re-filling a portable vaporizing device 100 and/or cartridges 112 for forming an inhalable vapor from vaporizable products, such as aromatic products, therapeutic products and/or products with physiological effects. Examples of such products can include herbs, such as tobacco, cannabis, lavender, chamomile, and other types of plant material. In one embodiment, a vaporizable product can comprise a cannabinoid, such as for example one or more of cannabidiol (a generally non-psychoactive therapeutic substance) and tetrahydrocannabinol (THC) (a psychoactive therapeutic substance). The vaporizable products may in some embodiments be in the form of an oil and/or wax product comprising the vaporizable products, e.g., as extracted from plant material containing the products, and may optionally be provided in combination with carriers or other additives. According to one aspect, the vaporizable products may be hash, which is a viscous resin containing tetrahydrocannabinol and other cannabinoids, extracted from the cannabis plant. According to yet another aspect, the vaporizable products may be cannabidiol in an oil or other liquid form. According to yet a further aspect, the vaporizable products can comprise a distillate product formed by distillation of an extract from the cannabis plant, typically in an oil and/or liquid form. In certain embodiments, the vaporizable product may be one that has a relatively high viscosity, such as a product having a viscosity of at least 5 Poise, and even at least 10 Poise or higher at room temperature.

Referring to FIGS. 1A-1C and 13A-13B, embodiments of a portable vaporizing device 100 for inhalation of a vaporizable product are shown. The device 100 comprises a vaporizable product receiving chamber 114 configured to receive a vaporizable product therein. According to certain embodiments, the device 100 is capable of being used with one or more cartridges 112 having the product receiving chamber 114 therein. The cartridges 112 may be removable and/or refillable, or can comprise single-use cartridges. In another embodiment, the device 100 can comprise a permanent product receiving chamber incorporated into the structure thereof, and which is not intended for removal from the device 100 but that may optionally be refilled with product. According to yet another embodiment, the cartridge itself can be considered to be a portable vaporizing device 100, that can be utilized either by itself (e.g., in an embodiment where the cartridge contains a built in heater), or with a complementary device to provide heating of the product within the cartridge 112 and any other components to facilitate inhalation of the vapor formed from the vaporizable product. Without being limited thereto, examples of suitable portable vaporizing devices 100 that may be filled and/or refilled according to the methods and/or systems herein, are described in U.S. Pat. No. 11,129,417 to Puff Corporation, issued on Sep. 28, 2021, which is hereby incorporated by reference herein in its entirety.

Figure 3A:
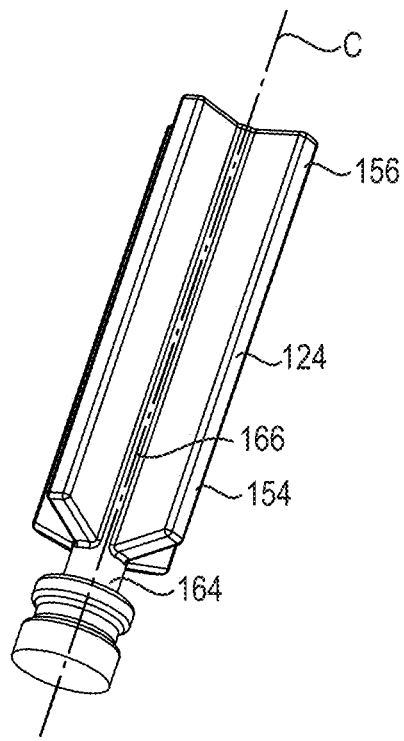
FIGS. 3A-3C are isometric views of different embodiments of heat transfer elements for a vaporizable product, according to aspects herein.
Figure 3B:
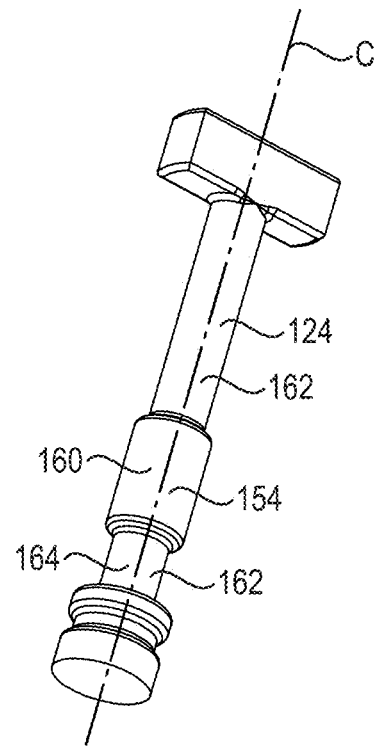
Figure 3C:
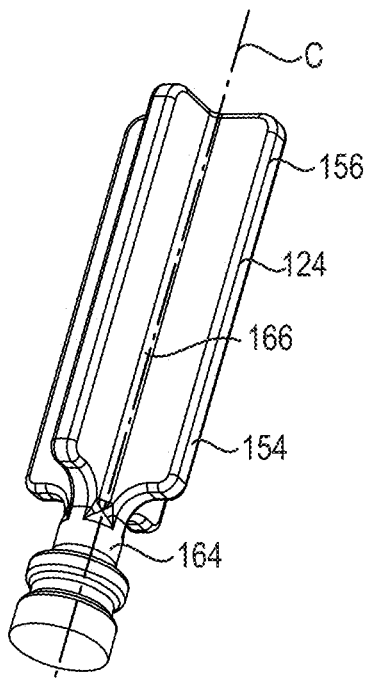
Figure 4A:
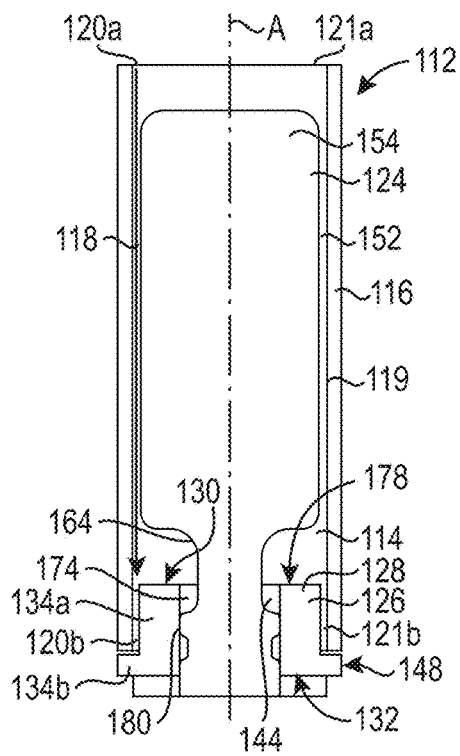
FIGS. 4A-4C are sectional views of different embodiments of cartridges according to aspects herein.
Figure 4B:
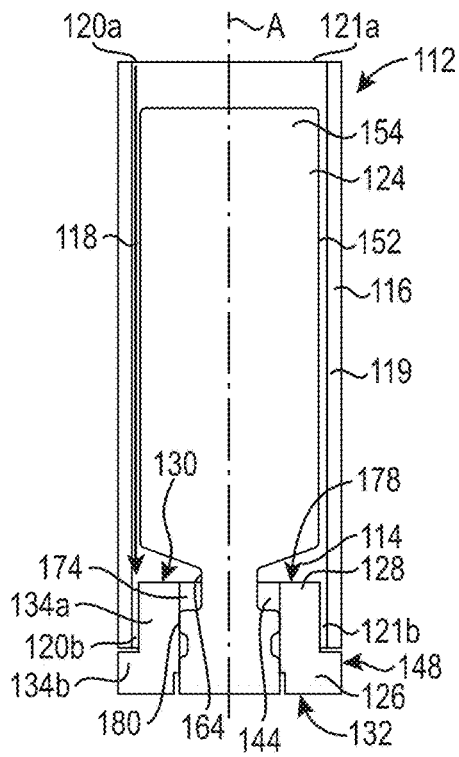
Figure 4C:
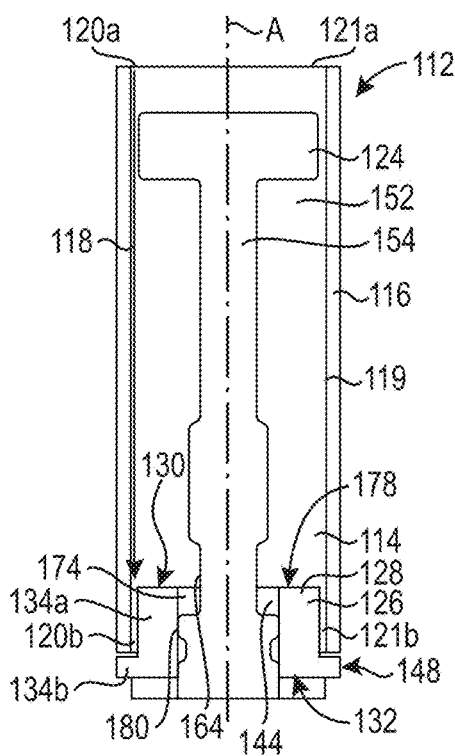
Figure 5A:
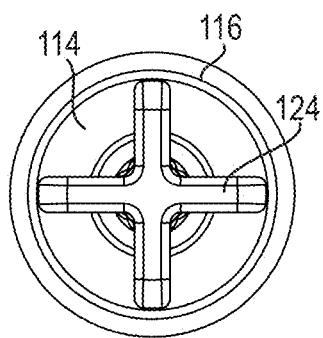
FIGS. 5A-5C are top views of the cartridge embodiments depicted in FIGS. 4A-4C, FIGS. 6A-6C are side views of the cartridge embodiments depicted in FIGS. 4A-4C, FIGS. 7A-7C are isometric views of the cartridge embodiments depicted in FIGS. 4A-4C.
Figure 5B:
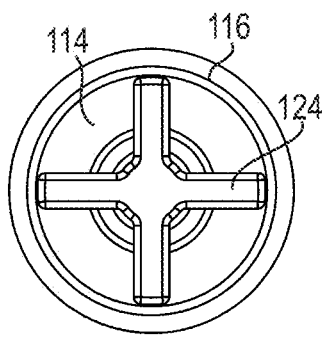
Figure 5C:
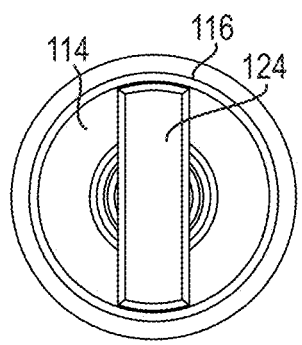
Figure 6A:
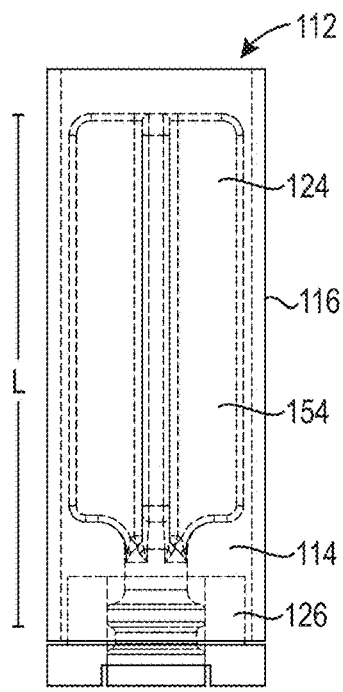
Figure 6B:
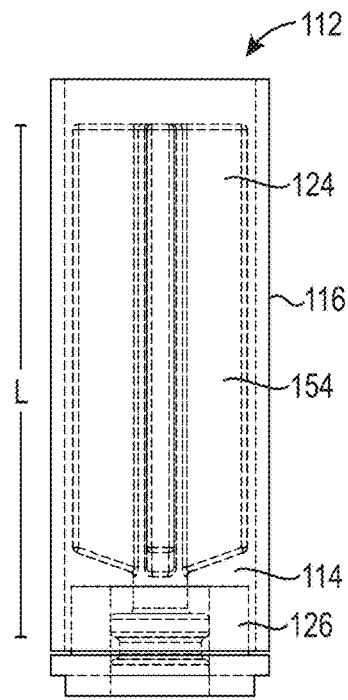
Figure 6C:
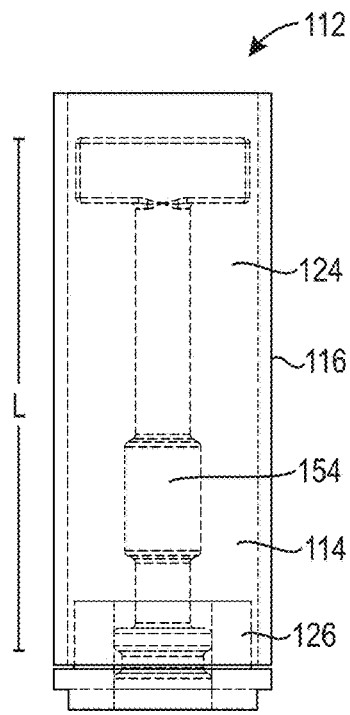
Figure 7A:
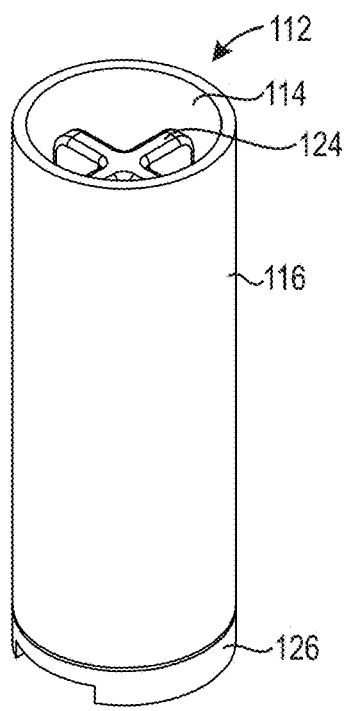
Figure 7B:
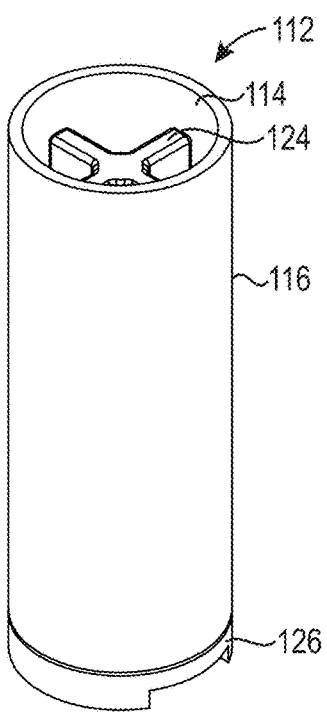
Figure 7C:
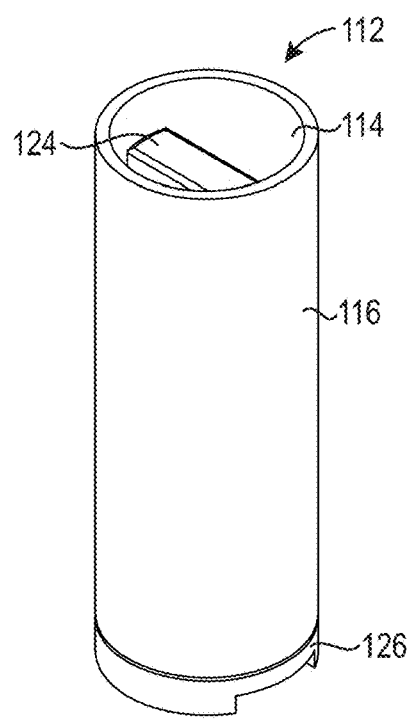
Figure 8A:
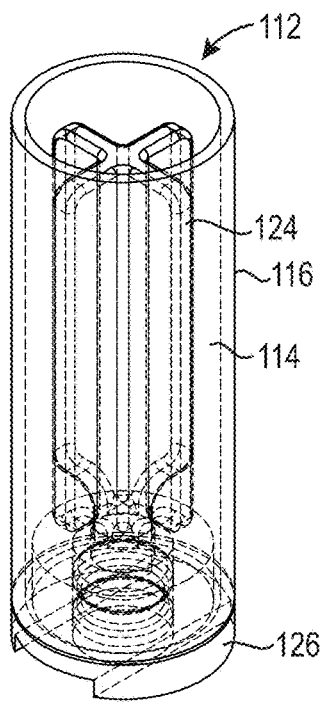
FIGS. 8A-8C are alternative isometric views of the cartridge embodiments depicted in FIGS. 7A-7C, FIGS. 9A-9C are profile views of different embodiments of heat transfer elements according to aspects herein.
Figure 8B:
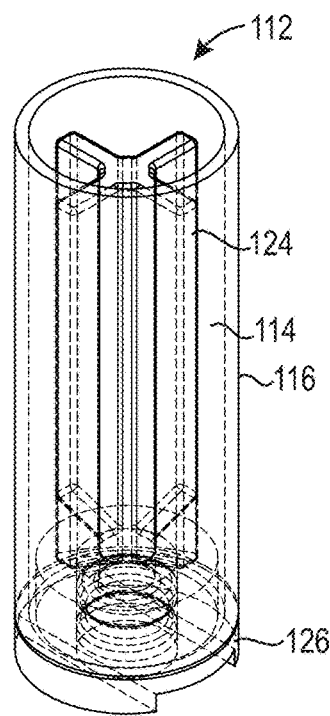
Figure 8C:
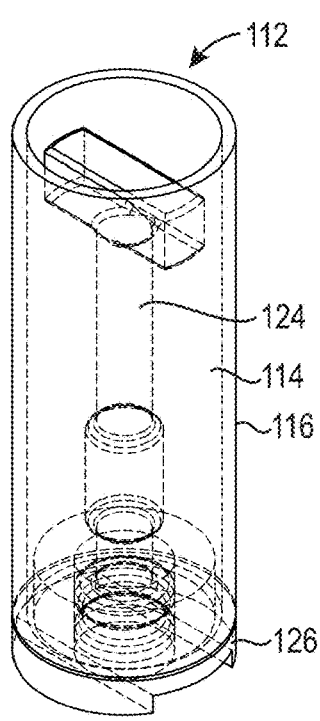
Figure 9A:
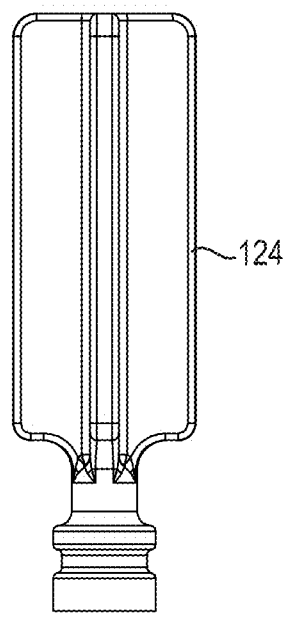
Figure 9B:
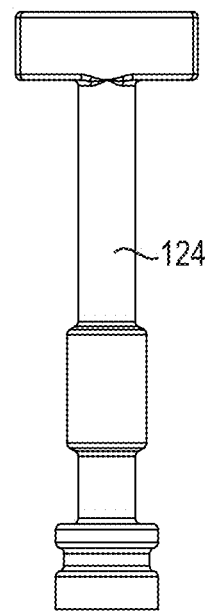
Figure 9C:
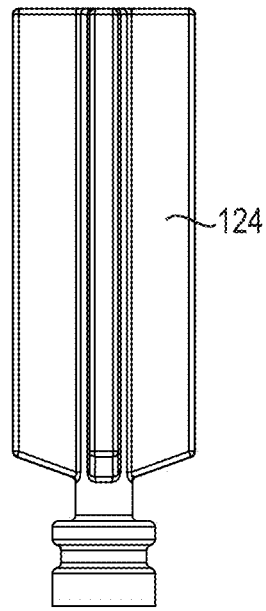

Referring to the embodiments as shown in FIGS. 1A-9C, the portable vaporizing device 100 and/or cartridge 112 comprises the vaporizable product receiving chamber 114 comprises one or more chamber walls 116 defining a product flow path 118 between upper and lower opposing ends 120a, 120b of the vaporizable product receiving chamber (see, e.g., FIGS. 1A-1C and 4A-4C). In the embodiments as shown in FIGS. 1A-1C, the chamber walls 116 comprise sidewalls 122 in a tube shape surrounding a circumference of the product receiving chamber 114, although other shapes for the sidewalls may also be provided, such as rectangular, prismatic, or irregular shapes. The chamber walls 116 can further define an upper opening 121a of the product chamber at the upper end 120a of the chamber 114, and a lower opening 121b at the lower end 120b of the product chamber 114 (see, e.g., FIGS. 4A-4C). The product flow path 118 generally extends from the upper end 120a of the product chamber 114 to the lower end 120b of the product chamber, and corresponds to the path taken by the product in the chamber as it moves via gravitational pull from the upper to the lower end of the product chamber. While the product flow path 118 as shown in FIGS. 4A-4C is depicted as being fairly linear from the top to the bottom end of the product chamber, the product flow path 118 can also in certain embodiments be convoluted, such as in a spiral, zig-zag, or other flow architecture, according to a design of the device 100. According to certain embodiments, the product chamber may be configured such that it can be filled with vaporizable product at the upper opening 121a, and such that the vaporizable product flows upon activation of the vaporizing device 100 towards the lower opening 121b.

Referring again to the embodiments of FIGS. 1A-1C and 4A-4C, the device 100 and/or cartridge 112 can comprise a heat transfer element 124 that extends at least partly along the product flow path 118 in the product chamber 114. The heat transfer element 124 is configured to transfer heat to a vaporizable product received in the product receiving chamber 114, to at least partially melt and/or reduce the viscosity of vaporizable product as it flows via gravitational pull from the upper end 120a to the lower end 120b of the chamber 114 along the product flow path 118. That is, in the case of vaporizable substances such as hash, cannabidiol and/or distillate, or other flowable substances, the heat transfer element 124 may be capable of heating the product within the product chamber 114, such that the product can be made flowable and/or be maintained in a flowable form as it passes along the product flow path 118. The flow path may be a substantially linear flow path, or can comprise a convoluted flow path from the upper end to the lower end of the product chamber.

According to certain embodiments, the device 100 and/or cartridge 112 comprises a porous valve element 126 located towards the lower end 120b of the chamber 114. The porous valve element 126 may form at least a portion of a bottom wall of the product receiving chamber 114, to contain the vaporizable product within the chamber 114 when the device 100 is not in operation. Referring to FIGS. 4A-4C and 10, the porous valve element 126 comprises a porous valve body 128 formed of a porous material configured to allow heated vaporizable product having a predetermined viscosity to pass therethrough.

That is, according to certain embodiments, the porous valve body 128 may have a porosity and/or pore size that allows vaporizable product to pass thorough the pores of the body when the product reaches a sufficiently low viscosity through heating thereof, or the product otherwise has a sufficiently low viscosity. For products such as distillate, the amount of heating required may be relatively little, as the viscosity of the product drops quickly with increasing temperature. However, for higher viscosity products, such as for example hash and cannabidiol, heating to higher temperatures may be required to reach a sufficiently low viscosity. In this way, in certain embodiments, the porous valve body 128 may act as a valve structure that allows product therethrough when an appropriately low viscosity is achieved, but contains product within the chamber when the viscosity exceeds a predetermined viscosity at which the product is able to pass through the pores of the porous valve body. In alternative embodiments, such as for very low viscosity products capable of passing through the porous valve body at room temperature or with substantially no heating, an alternative mechanism for containing a flow of the product from the chamber may be provided. The porous valve element 126 can absorb product having the predetermined viscosity via capillary action, and this capillary action may also serve to contain the product within or outside of the porous valve element 126 when it is not activated (e.g., when it is not being heated)

Referring again to the embodiments as shown in FIGS. 4A-4C and 10, the porous valve element 126 further comprises at least one first porous entry surface 130 of the porous valve body 128 configured to receive the heated vaporizable product from the product flow path 118 into the porous valve body 128. As depicted in the embodiments of FIGS. 4A-4C, the first porous entry surface comprises a substantially planar surface that is configured to contact the product at the lower end 120b of the product chamber 114, although alternative embodiments for the first entry surface may also be provided. The porous valve element 126 also comprises at least one porous vaporizing surface 132 of the porous valve body 128 that is configured to flow the heated vaporizable product out of the porous valve body 128. In the embodiment shown in FIGS. 4A-4C and 10, at least a portion of the porous vaporizing surface 132 is on an opposite side of the valve body 128 from the first porous entry surface 130.

Furthermore, in the embodiment as depicted in these FIGS. 4A-4C, at least a portion of the porous valve body 128 is configured to be fitted within the walls 116 of the product chamber 114, and at least a portion of the porous valve body 128 extends beyond the walls 116 of the product chamber 124, such that least a portion of the porous vaporizing surface 132 may extend beyond the walls 116 of the product chamber. In the embodiment as shown in FIGS. 4A-4C, the porous valve body comprises an upper portion 134a that is sized to fit within the walls 116, and a lower portion 134b that extends beyond the walls 116 and also has a greater width than the walls 116. For example, the lower portion 134b may form a lower lip that extends both below and beyond a width of the walls 116. In the embodiment shown in FIGS. 4A-4C and 10, the valve body 128 comprises a generally annular shape, with an upper portion 134a comprising an upper ring-shaped portion having a first diameter sized to fit within the walls 116, and a lower portion 134b comprising an lower ring-shaped portion having a second diameter than is larger than the first, and that exceeds a diameter of the walls 116. For example, the lower ends of the walls 116 may abut a top surface of the lower portion of the valve body, such that it can act to plug the lower end of the product chamber 114. Other configurations and/or shapes may also be provided, such as rectangular and/or square shapes for the wall and/or valve body cross-section.

Referring to FIGS. 12A-12D, according to embodiments herein, at least one or both of the heat transfer element 124 and porous valve element 126 are configured to be placed in thermal contact with at least one heating element 136, such as the same or different heating elements 136. In one embodiment, the at least one heating element 136 may be a part of a removable cartridge 112 that is provided to the vaporizing device. That is, the at least one heating element 136 may be removable as a part of the cartridge from the vaporizing device 100. In another embodiment, the heating element 136 forms a part of the vaporizing device 100, and a removable cartridge 112 having the porous valve element 126 and/or heat transfer element is configured to be received within the vaporizing device in a configuration such that the porous valve element 126 and/or heat transfer element 124 are placed into thermal contact with the at least one heating element 136 in the vaporizing device 100 (see, e.g., FIG. 13A).

According to embodiments herein, one or both of the heat transfer element 124 and porous valve element 126 can be placed into thermal communication with the at least one heating element 136 to provide heating of the heat transfer element 124 and porous valve element 136 during operation of the portable vaporizing device 100, such as to heat the vaporizable product to the predetermined viscosity at which the vaporizable product is capable of flowing through the porous valve element, and/or to provide a predetermined rate of flow through the porous valve element 126. For example, the porous valve element 126 can be configured to be heated by the at least one heating element 136 to cause the heated vaporizable product having the predetermined viscosity from the product receiving chamber 114 to flow into and through the porous valve body 128. The porous valve element 126 can also be configured such that the heated vaporizable product flowing through the porous valve body at least partially vaporizes in the vicinity of the at least one porous vaporizing surface 132 while exiting the porous valve body 128, thereby creating a vaporized product suitable for inhalation. In one embodiment, one or both of the porous valve element and heat transfer element are placed into direct physical contact with the at least one heating element, which may be the same or different heating elements, in order to transfer heat from the heating element(s) to the porous valve element and heat transfer element.

According to one embodiment, the heat transfer element 124 is configured to be heated by the at least one heating element 136 at a position of the heat transfer element 124 along the product flow path 118 to a predetermined temperature of at least 125° C., and even higher, to provide the predetermined viscosity of the vaporizable product in the chamber 114. For example, according to certain embodiments, the heat transfer element is configured to be heated at the position along the product flow path to a predetermined temperature of at least 125° C., at least 135° C., a least 145° C., at least 150° C., at least 165° C., at least 170° C., at least 180° C., at least 195° C., at least 200° C., at least 215° C., at least 225° C., and/or at least 250° C., to heat the vaporizable product in the product chamber. Furthermore, according to one embodiment, the heat transfer element 124 is configured to be heated at the position along the product flow path 118 to the predetermined temperature within a time period of no more than 10 seconds, no more than 25 seconds, no more than 50 seconds, no more than 75 seconds, no more than 100 second, and/or no more than 150 seconds. In one embodiment, the predetermined temperature may be obtained within 1 heating cycle and no more than 3 heating cycles ("hits"), during which power is applied to the heating element(s) to heat the valve element and/or heat transfer element, which heating cycle(s) may have a duration of about 10 seconds each. Thus, the heat transfer element 124 can be configured in certain embodiments to provide rapid heating of the vaporizable product to achieve and maintain flowability of the vaporizable product in the product chamber 114. According to yet another embodiment, the heat transfer element 124 is configured to be heated at the position along the product flow path 118 to achieve a change in temperature at the predetermined position, as compared to prior to heating onset, of at least 50° C., at least 60° C., at least 75° C. and/or at least 100° C., in no more than 10 seconds, no more than 25 seconds, no more than 50 seconds, no more than 75 seconds, no more than 100 seconds, and/or no more than 150 seconds.

According to one embodiment, the position on the heat transfer element 124 at which the predetermined temperature is achieved is at one or more of a top end 138a of the heat transfer element and an area of the surface 140 along the length L of the heat transfer element 124 (see, e.g., FIGS. 1A-1C). For example, the position at which the predetermined temperature is achieved can extend along at least 10%, at least 25%, at least 50%, at least 75%, at least 90%, and/or at least 95% of the length L of the heat transfer element 124.

According to one embodiment, the porous valve element 126 is configured such that the at least one first porous entry surface 130 of the porous valve body 128 is configured to be heated to a predetermined temperature of at least 125° C., at least 135° C., a least 145° C., at least 150° C., at least 165° C., at least 170° C., at least 180° C., at least 195° C., at least 200° C., at least 215° C., at least 225° C., and/or at least 250° C. Furthermore, according to certain embodiments, the porous valve element is configured to be heated such that the at least one first porous entry surface 130 of the porous valve body, and/or the vaporizing surface, is heated to the predetermined temperature within a time period of no more than 10 seconds, no more than 25 seconds, no more than 50 seconds, no more than 75 seconds, no more than 100 seconds, and/or no more than 150 seconds. According to yet another embodiment, the porous valve element is configured such that a change in temperature at the at least one first porous entry surface 130 and/or vaporizing surface achieves a change in temperature as compared to prior to heating onset of at least 50° C., at least 60° C., at least 75° C. and/or at least 100° C., in no more than 10 seconds, no more than 25 seconds, no more than 50 seconds, no more than 75 seconds, no more than 100 seconds, and/or no more than 150 seconds.

Furthermore, according to certain aspects, the device 100 and/or cartridge having the heat transfer element and/or porous valve element is configured to heat the vaporizable product during operation of the device to a temperature of at least 125° C., 135° C., a least 145° C., at least 150° C., at least 165° C., at least 170° C., at least 180° C., at least 195° C., at least 200° C., at least 215° C., at least 225° C., and/or at least 250° C. The heat transfer element and/or porous valve element can be configured to heat the vaporizable product during operation of the device to such temperatures along at least 25%, at least 35%, at least 50%, at least 65%, at least 75%, at least 85% and/or at least 90% of the major flow axis through the product receiving chamber.

According to certain embodiments, the predetermined viscosity of the vaporizable product in the vicinity of the at least one first porous entry surface 130, as heated by one or more of the heat transfer element 124 and porous valve element 126, is significantly less than a room temperature viscosity of the vaporizable product. For example, the predetermined viscosity may be no more than 20 Poise, no more than 18 Poise, no more than 15 Poise, no more than 10 Poise, no more than 5 Poise, no more than 2 Poise, no more than 1.5 Poise, no more than 1.25 Poise, no more than 1 Poise, no more than 0.75 Poise, and/or no more than 0.5 Poise. For example, a viscosity of a hash material may be about 10 P when heated to a temperature of 195° C., and for a less viscous cannabidiol material, the viscosity when heated to this temperature may be about 1 P.

Returning to FIGS. 12A-12D, in one embodiment, at least a part of the at least one porous vaporizing surface 132 is a same surface that is configured to be placed in thermal contact with the at least one heating element 136. That is, a same surface at which the vaporizable product exits the porous valve body 128 may be a same surface that is in thermal contact with the at least one heating element, to provide heating at the vaporizing surface. For example, referring to the embodiment in FIGS. 12A-12D, at least a portion of the vaporizing surface 132 is on an opposing surface of the porous valve body 128 from the first porous entry surface 130. The portion of the vaporizing surface 132 is placed in contact with a heating element 136 to provide heating of the surface. In the embodiment shown in FIG. 12A, the heating element 136 is provided in contact with an interior surface portion 142 of the vaporizing surface 132 that is a part of an aperture 144 extending inside a central region of the porous valve element 126. In the embodiment shown in FIGS. 12B-12D, the portion of the vaporizing surface 132 that is opposite the porous entry surface 130 (e.g., that portion of the vaporizing surface 132 parallel to the porous entry surface 13) is placed in contact with the heating element 136, to transfer hear to the valve element 126 via that portion of the vaporizing surface 132.

According to one embodiment, the flow of the vaporizable product through the product chamber and to the porous valve element 126 can be configured to provide an optimum flow of the vaporizable product for generation of vapor for inhalation. For example, referring to FIGS. 4A-4C, the components of the cartridge 112 and/or device 100 may be configured such that a net flow direction of the vaporizable product into the at least one first porous entry surface 130 of the porous valve body 128 is aligned with and/or no more than 45° offset from a major axis of flow of the vaporizable product through the product receiving chamber. The major axis of flow may be the net direction that the product flows through the product receiving chamber, such as in a direction extending from the top end to the bottom end of the product receiving chamber 114 as shown in FIGS. 4A-4C. That is, the first porous entry surface may be substantially and even entirely perpendicular to the major axis of flow of the vaporizable product through the product chamber, and/or substantially perpendicular to a longitudinal axis A of the product chamber 114. For example, in a case where a major axis of flow of the vaporizable product is along a longitudinal direction of the product receiving chamber, and at least a portion of the at least one porous vaporizing surface of the porous valve element can be substantially perpendicular to and/or at least 45° offset from the major flow axis. Furthermore, in another embodiment, the porous valve can comprise an annular ring about a periphery of the product chamber at the lower end thereof, in which case a flow of the product may be downwards through the product chamber, and then laterally through the porous valve element surrounding the sides of the product chamber at the lower end.

Figure 10:
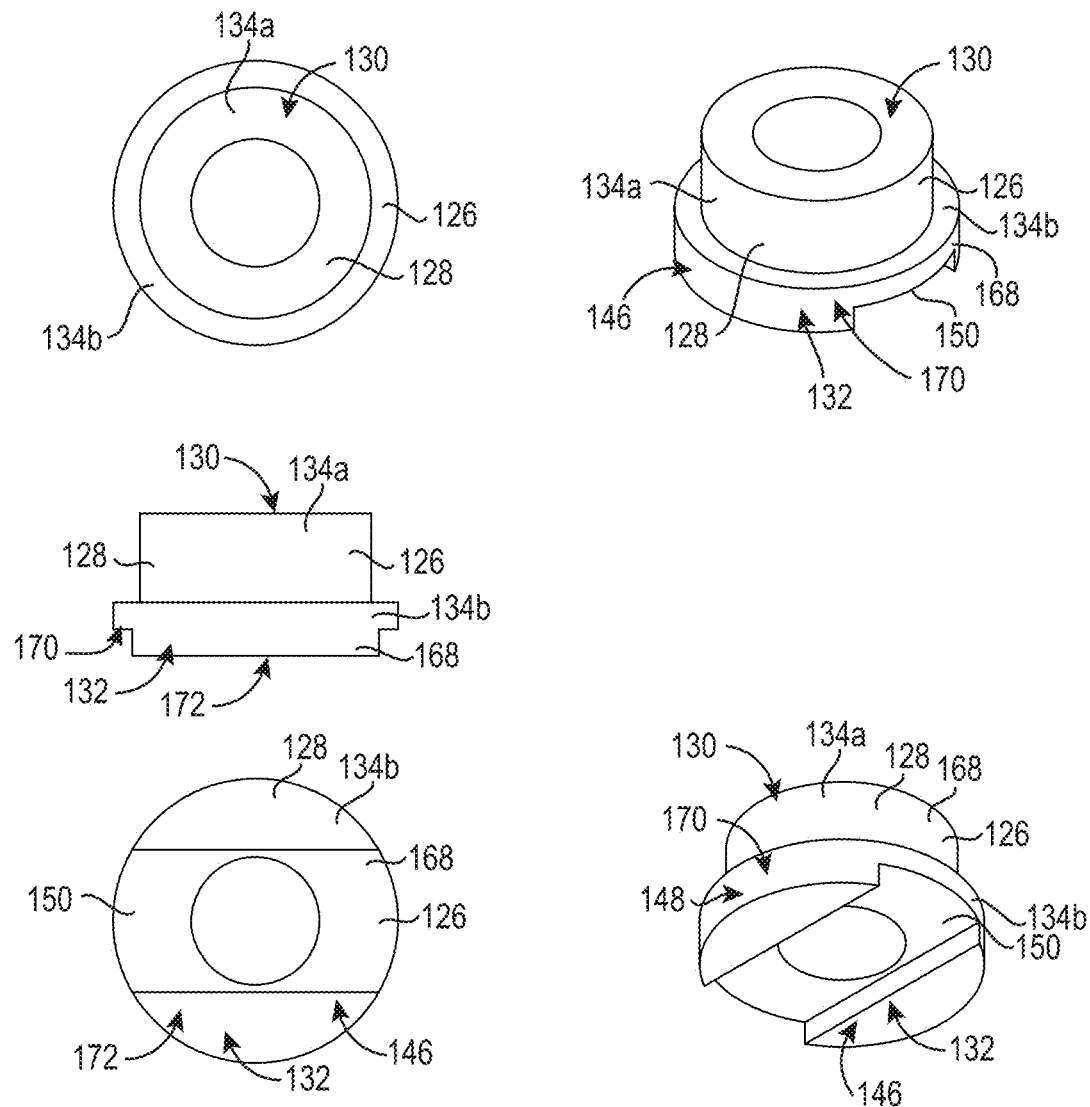
FIG. 10 depicts views of an embodiment of a porous valve element according to aspects herein.

According to certain embodiments the porous vaporizing surface 132 of the porous valve element 126 comprises a first surface 146 that is substantially perpendicular to a major axis of flow of the vaporizable product along the longitudinal direction of the product receiving chamber 114, at least a portion of which first surface 146 is configured to be placed in thermal contact with the at least one heating element 136 (see, e.g., FIG. 10). The porous vaporizing surface 132 can further comprise one or more second surfaces 148 at which the vaporizable product can exit the porous body, but which are not placed in thermal contact with the heating element 136. For example, the porous vaporizing surface 132 can comprise one or more second surfaces 148 located about a periphery of the porous valve body through which vaporizable product can exit the porous valve body. The surface area of the first surface 146 that is placed in thermal contact with the heating element may also be selected to provide good heating of the porous valve element. For example, the heating element 136 may be placed in contact with a planar section of the first surface opposing the porous entry surface of the porous valve body, and may be in contact with at least 50%, at least 65%, at least 75%, at least 85%, at least 90%, at least 95%, and/or substantially the entirety of the planar opposing section of the vaporizing surface, wherein the planar section of the first surface opposing porous entry surface has a surface area of at least 10 mm$^2$, at least 15 mm$^2$, and/or at least 18 mm$^2$. Furthermore, even in case where the first surface has channels or grooves formed therein, an area of the first surface about the grooves and/or channels that makes contact with the heating element may be at least 10 mm$^2$, at least 15 mm$^2$, and/or at least 18 mm$^2$. The dimensions of the porous valve element can also be selected to provide good heating, for example a thickness of the porous valve body as measured between the first surface of the porous vaporizing surface and the at least one first porous entry surface, is at least 1.5 mm, at least 2 mm, and/or at least 3.5 mm, and no more than 10 mm, no more than 8 mm, and/or no more than 4 mm.

According to one embodiment, at least a portion, and even the entirety, of the at least one first porous entry surface 130 of the porous valve body is configured to be exposed to the vaporizable product in the product receiving chamber 114. That is, the first porous entry surface may be in direct contact with the vaporizable product in the chamber, without any intervening layers (e.g., without a separate cotton or other wicking layer in between the surface and product), such that the product enters the entry surface 130 directly upon heating to the predetermined temperature, without passing through any other filtering or cover materials. That is, the first porous entry surface is uncovered and is in direct contact with the vaporizable product in the product chamber.

Referring to the embodiments as shown in FIGS. 4A-4C, the heat transfer element 124 can extend beyond the at least one first porous entry surface 130 of the porous valve body, such as into an interior region 152 of the product receiving chamber 114. In one embodiment, the heat transfer element 124 can extend along a central axis A of the product chamber, such as along the major flow axis of product through the product receiving chamber. In yet another embodiment, the heat transfer element 124 can extend along the exterior of the product chamber 114, such as adjacent to or as a part of the sidewalls 112 defining the product chamber 114. According to one embodiment, the heat transfer element may extend along at least 25%, at least 35%, at least 50%, at least 65%, at least 75%, at least 85%, and/or at least 90% of the major flow axis through the product receiving chamber. A length of the product receiving chamber along the major flow axis, according to certain aspects, can be at least at least 10 mm, at least 15 mm, and/or at least 20 mm, such as about 22 mm. In the embodiments as shown in FIGS. 4A-4C, the heat transfer element 124 extends along substantially the entire length of the product chamber 114, from a position close to the upper end 120a of the product chamber, to at least the porous valve element 126. In the embodiments as shown in FIGS. 4A-4C, the heat transfer element 124 further extends through a central aperture 144 in the porous valve element 126 to allow thermal contact of the bottom end 138b of the heat transfer element with a heating element 136 to heat the heat transfer element 124.

According to certain embodiments, the porous valve body 128 of the porous valve element 126 comprises a porous material that provides suitable heat transfer characteristics to heat the vaporizable product in the product receiving chamber 114. For example, according to one embodiment, the porous valve element 126 comprises a porous body 128 having a porous material comprising at least one selected from the group consisting of porous glass, porous ceramic, porous quartz, and porous sintered metal. As yet another example, the porous valve element 126 can comprise a porous body 128 having a porous material comprising at least one selected from the group consisting of porous borosilicate glass, porous alumina, and porous silicon carbide. As yet another example, the porous valve element 126 can comprise a porous body 128 having a porous material comprising porous borosilicate glass. According to certain aspects, the porous valve body 128 may be formed of a material having a sufficiently high thermal conductivity, to provide for heating of the valve body 128 and transfer of heat to the vaporizable product. In one embodiment, the porous valve body comprises a porous material having a thermal conductivity of at least 0.5 W/m*K, at least 0.8 W/m*K, at least 1 W/m*K, at least 1.15 W/m*K, and/or at least 1.2 W/m*K. In yet a further embodiment, the thermal conductivity may be at least 10 W/m*K, at least 15 W/m*K, at least 30 W/m*K, at least 50 W/m*K, and/or at least 70 W/m*K. According to certain embodiments, the thermal conductivity of the porous valve body 128 may be less than 300 W/m*K, less than 200 W/m*K, less than 100 W/m*K, less than 50 W/m*K, less than 25 W/m*K, less than 10 W/m*K, and/or less than 5 W/m*K. For example, the thermal conductivity may be in the range of from 0.5 to 5 W/m*K, such as 1.0 to 2.0 W/m*Km, and/or may be in a range of from 10 to 50 W/m*K, such as from 15 to 27 W/m*K, and/or may be in a range of from 50 to 200 W/m*K, such as from 70 to 170 W/m*K. Furthermore, according to certain aspects, the porous valve body 128 can comprise a specific heat of less than 1200 J/kg*K, less than 1000 J/kg*K, and/or less than 900 J/kg*K, and greater than 500 J/kg*K, greater than 750 J/kg*K, and/or greater than 800 J/kg*K.

According to certain aspects, a porosity of the porous valve body 128 and/or the pore size of the porous valve body may be selected to provide for a flow of the vaporizable product through the porous valve element. For example, a porosity of the porous valve element may be at least 25%, at least 35%, and/or at least 50%, and less than 95%, less than 85% and/or less than 75%. As another example, the pore size may be selected such that the porous valve body has an average pore size of at least 2 microns, at least 3 microns, at least 4 microns, at least 5 microns, at least 8 microns, and/or at least 10 microns, and less than 25 microns, less than 18 microns, less than 16 microns, less than 10 microns and/or less than 8 microns. As another example, the average pore size may be in the range of from 2 microns to 20 microns, such as from 2 microns to 8 microns, and even from 3 to 6 microns, such as from 4 microns to 5.5 microns, and as another example may be in the range of from 8 microns to 20 microns, such as from 10 microns to 16 microns. The porosity and/or pore size may also be selected at least in part in relation to a vaporizable product to be used in the device. For example, in the case of a thicker and/or more viscous product, such as hash, the porosity and/or pore size may be selected to be on the larger side, to provide for a suitable flow of the material through the porous valve element. As another example, in the case of a less viscous product, such as distillate, a lower porosity and/or pore size may be selected to control flow through the porous valve body.

According to certain embodiments, the heat transfer element 124 comprises a material selected to provide suitable thermal characteristics for the transfer of heat to the vaporizable product in the chamber 114. According to certain aspects, the heat transfer element 124 is substantially non-porous and/or has a porosity that is less than that of the porous valve body 128. The heat transfer element 124 can also be selected of the same or a different material than the porous valve body. For example, according to certain embodiments, the heat transfer element comprises at least one selected from a glass, a ceramic, and a metal. As yet another example, the heat transfer element can comprise a material corresponding to at least selected from the group consisting of alumina, silicon carbide, stainless steel, titanium, aluminum, graphite and aluminum nitride. In yet another example, the heat transfer element can comprise a material corresponding to at least one selected from the group consisting of alumina and silicon carbide. In one embodiment, the heat transfer element 124 can comprise a body having a thermal conductivity of at least 0.5 W/m*K, at least 0.8 W/m*K, at least 1 W/m*K, at least 1.15 W/m*K, and/or at least 1.2 W/m*K. For example, the thermal conductivity may be at least 10 W/m*K, at least 15 W/m*K, at least 30 W/m*K, at least 50 W/m*K, at least 70 W/m*K, at least 100 W/m*K, at least 125 W/m*K, at least 150 W/m*K and/or at least 160 W/m*K. According to certain embodiments, the thermal conductivity of the heat transfer element 124 may be less than 300 W/m*K, less than 200 W/m*K, less than 100 W/m*K, less than 50 W/m*K, and/or less than 25 W/m*K. For example, a thermal conductivity of the heat transfer element 124 may be in the range of from 10 to 300 W/m*K, such as from 10 to 35 W/m*K, and even 15 to 27 W/m*K, such as from 50 to 200 W/m*K, including 70 to 170 W/m*K, such as from 10 to 20 W/m*K, including about 12-16 W/m*K, such as from 20 to 30 W/m*K, including 23 to 26 W/m*K, such as from 160 to 245 W/m*K, including 164-237 W/m*K, such as from 160-175 W/m*K, including 165 to 170 W/m*K, and/or such as from 130 to 195 W/m*K, including 140 to 180 W/m*K. Furthermore, according to certain embodiments, the heat transfer element comprises a body having a specific heat of less than 1200 J/kg*K, less than 1000 J/kg*K, and/or less than 900 J/kg*K, and greater than 500 J/kg*K, greater than 750 J/kg*K, and/or greater than 800 J/kg*K.

Furthermore, according to certain embodiments, the materials suitable for the heat transfer element 124 may also be suitable for use as the material for the porous valve body when provided in a porous form.

Referring to the embodiments of FIGS. 3A-3C, 4A-4C and 6A-6C, according to certain aspects, the heat transfer element 124 comprises an elongate heat-conducting column 154 that extends along a predetermined length L of the vaporizable product receiving chamber 114. In these embodiments as shown, the elongate heat-conducting column 154 is disposed within the product chamber 114. In other embodiments, the elongate heat-conducting column is disposed externally to the product chamber 114, and/or comprises one or more sidewalls 122 of the vaporizable chamber 114. The elongate heat-conducting column 154 may heat the product along the product flow path to reduce the viscosity and/or at least partially melt the product, for example to maintain flowability of the product in the chamber.

Referring to FIGS. 3A-3C, according to certain embodiments, the structure and configuration of the elongate heat-conducting column 154 can be selected to provide predetermined heat characteristics with the product chamber 114. For example, referring to FIGS. 3A and 3C, according to one embodiment, the elongate heat-conducting column comprises a plurality of fins 156 extending radially outwardly from a central axis C of the elongate heat-conducting column. For example, the elongate heat-conducting column can comprises 4 fins that are positioned substantially equidistant about the central axis C of the elongate heat-conducting column, and that extend outwardly from the central axis of the elongate heat conducting column, and where the fins further extend longitudinally along a length of the column and/or product receiving chamber 114. The fins 156 may provide an increased surface area structure that provides greater thermal contact with the vaporizable product as it passes through the product chamber. The shape and size of the fins can also be selected in accordance with desired heating characteristics, as well as in relation to the material used for the column and product characteristics. For example, referring to FIG. 3A, which may be an embodiment suitable for a cannabidiol product, the fins may extend a significant distance down the length of the column, as compared to FIG. 3C depicting an embodiment suitable for a hash product, where a higher thermal conductivity column may have fins that terminate slightly more highly above the end of the column, to provide a space above the porous valve element. Other configurations of the fins may also be provided, including more or fewer fins, shorter fins, longer fins, thicker or thinner fins, etc. Also, alternate high surface area structures other than fins can be provided, such as spiral features or projections that extend from the column 154. In one embodiment, the plurality of fins extend at least 25%, at least 50%, at least 75%, at least 80% and/or at least 95% along the length of the product receiving chamber, to provide heating of the product in the product chamber. Furthermore, according to certain embodiments, the plurality of fins comprise portions that extend at least 25%, at least 50%, at least 75%, at least 85% and/or at least 95% of a cross-sectional width of the product receiving chamber, such as across a diameter of the product receiving chamber.

Referring to FIG. 3B, in one embodiment, the elongate heat-conducting column 154 comprises a first section 158 comprising bulging portion 160 along a central axis of the elongate heat-conducting column 154, the bulging portion 160 comprising a greater radius from the central axis than one or more second sections 162 along the central axis of the elongate heat conducting column. The building portion 160 may serve to extend the column into the product flow path such that the vaporizable product is brought into contact with the column as it flows through the product chamber to heat the vaporizable product. The embodiment as shown in FIG. 3B may be suitable, for example for a lower viscosity material, such as distillate, which is to be heated but may not require as high of temperatures as cannabidiol or hash to flow through the porous valve element. Furthermore, in certain embodiments, the bulging portion 160 may only extend along a section of the product flow path in the chamber, and may not extend along the entire flow path. For example, the bulging portion 160 may be located towards the lower end of the column in a bottom section of the product chamber, so as to provide heating of the product before the product comes into contact with the porous valve element.

In one embodiment, referring to FIGS. 3A-3C and FIGS. 4A-4C, the elongate heat-conducting column 154 can comprises a neck region 164 towards the bottom end 138b of the column 154, and configured to be proximate to the porous valve element, along the central axis of the column. According to certain aspects, the neck region 164 has a thinner diameter than other regions of the column 154 along the central axis of the heat conducting column. According to some embodiments the neck region may provide less heating of the product in that region, for example to control a temperature of the product flowing from the upper end 120a of the product chamber towards the porous valve element 126, such that the product achieves the predetermined viscosity in the vicinity of the porous valve element. For example, the neck region may allow the product to cool slightly such that the flow of the product into the porous valve element can be controlled. In one version, the neck region 164 comprises a region where the elongate heat-conducting column tapers in diameter from a first maximum diameter to a second maximum diameter than is smaller than the first at the neck region proximate the porous valve element. For example, a diameter of the fins 156 may taper down to the diameter of a central column body 166 from which they extend, as shown in FIGS. 3A and 3B. In one embodiment, the elongate heat conducting column has a diameter or at least 2.5 mm, at least 3 mm and/or at least 3.5 mm proximate a base of the elongate heat conducting column and a diameter at a neck region of less than 4 mm, less than 3 mm and/or less than 2.5 mm. A length of the neck region may also be relatively small in comparison to a length of the column having the fins and/or other protruding region.

Without being limited to any one particular embodiment for any particular product, it is noted that FIGS. 2A-2B, 3A, 4B, 5B, 6B, 7B, 8B, and 9C, depict embodiments that may be suitable for a vaporizable product comprising cannabidiol. FIGS. 3B, 4C, 5C, 6C, 7C, 8C, and 9B, depict embodiments that may be suitable for a vaporizable product comprising distillate. FIGS. 3C, 4A, 5A, 6A, 7A, 8A and 9A depict embodiments that may be suitable for a vaporizable product comprising hash. However combinations of these structures may also be provided, and the structures may also be used with any vaporizable product.

Referring to FIGS. 4A-4C and 10, in one embodiment, the porous valve element 126 comprises an annular fitting 168 having a first or upper portion 143a comprising the porous entry surface 130, and which is configured to fit within the one or more walls 122 defining the product chamber 114. In one embodiment, the annular fitting 168 can further comprise a second or lower portion 143a that is configured to extend beyond the end of the one or more walls 122, such that the vaporized product can exit the chamber in a lateral direction via peripheral surfaces 170 of the lower portion. Alternatively and/or additionally, the vaporized product may exit the chamber through a base surface 172 of the annular fitting, where both the bottom surface and/or peripheral surfaces may form portions of the vaporizing surface 132 of the porous valve element. According to one embodiment, the second portion 143a of the porous valve body may have a peripheral region with a diameter greater than that of the first portion, wherein the vaporizable product travels through the first portion of the porous valve element to the second portion and the vapor formed from the vaporizable product exits the porous valve element through the one or more of a peripheral surface of the peripheral region, or through the surface 172 formed on the bottom of the second portion. According to yet another embodiment, the annular fitting 168 can comprise a single portion having substantially the same diameter throughout the thickness thereof, such as a disc-like ring, where the fitting 168 can either be fitted entirely within the sidewalls of the product chamber, or can at least partly extend from the product chamber. Furthermore, which an annular or ring-like fitting is described and shown, the porous valve element is not limited thereto, and may comprise further shapes, such as cuboid shapes or other shapes, and may be sized to accommodate a shape and/or structures within the product chamber, which may comprise a circular cross-section or other shapes, such as a rectangular cross-section or an irregular cross-sectional shape.

According to one embodiment, referring to FIG. 10 and FIGS. 4A-4C, the porous valve element can comprise an annular fitting 168 having a central aperture 144 formed therethrough (e.g. through a thickness thereof), wherein the central aperture 144 forms a reservoir 174 configured to receive the vaporizable product therein. For example, product flowing towards the porous valve element can collect in the reservoir 174 and may enter the porous valve body via one or more interior surfaces 176 on the interior of the aperture 144. The flow of the product into the porous valve body may thus be through porous entry surface 132 comprising the interior surface portion 176 and a top surface portion 178 that is perpendicular to the flow of the product through the chamber. According to one embodiment, the heat transfer element can comprises an elongate column having a bottom end or base 138*b* configured to fit through aperture 144 in the valve, such that it can be placed in thermal contact with the at least one heating element 136. The sides of the lower portion of the column can define the reservoir in cooperation with the internal surfaces of aperture in the porous valve element. Also, the heat transfer element can comprise one or more annular stopper rings 180 or other features that can be placed flush with the interior surfaces of the aperture, such as to block a flow of product through the aperture 144 and out of the chamber.

Figure 12A:
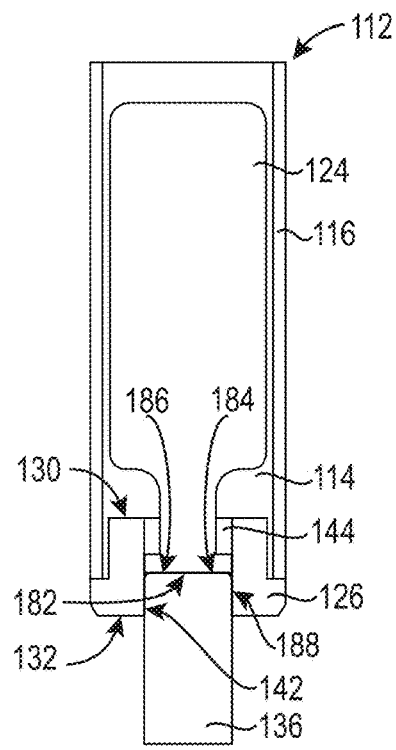
FIGS. 12A-12D are cross-sectional views of different embodiments of cartridges and heating elements to heat the cartridges, according to aspects herein.
Figure 12B:
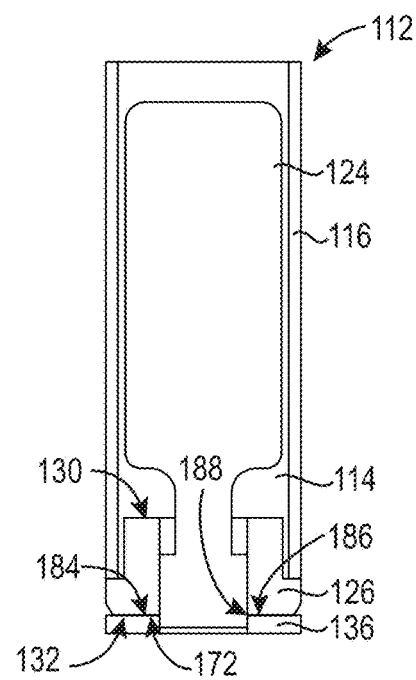

Referring to the embodiments of FIGS. 12A-12D, according to certain aspects, the heat transfer element 124 and porous valve element 126 are configured to be heated by the same heating element 136 or by different heating elements. For example, in the embodiments as shown in FIGS. 12A-12B, both the heat transfer element 124 and porous valve element 126 are heated by the same heating element, by being placed in thermal communication (e.g., direct physical contact) with the heating element 136. In the embodiment as shown in FIG. 12A, the bottom surface 182 of the heat transfer element is placed in direct contact with a surface 184 of a heating element 136, such as an upper surface 186 of a heating rod, and the interior portions 176 of the vaporizing surface 132 of the valve element, within the valve aperture, are contacted with a surface 184 corresponding to the side surface portions 188 of the heating element such as the side surfaces of the heating rod contacting the heat transfer element. Thus, the heat transfer element and porous valve element may be simultaneously heated by the same heating element. In the embodiment as shown in FIG. 12B, the heat transfer element comprises a side surface 190 that is placed in contact with a side surface portion 188 of the surface of a heating plate 136, the upper surface 186 of which heating plate is placed in contact with the bottom portion 172 of the vaporizing surface such that the porous valve element and heat transfer element are simultaneously heated by the heating plate. In the embodiment as shown in FIG. 12B, the heating plate comprises a donut shape, to at least partially encircle the base of the heat transfer element. As an alternative, the heating element 136 can comprise a heating plate that has an upper surface 186 that contacts the bottom surfaces of both the porous valve element and heat transfer element, to transfer heat thereto.

Figure 12C:
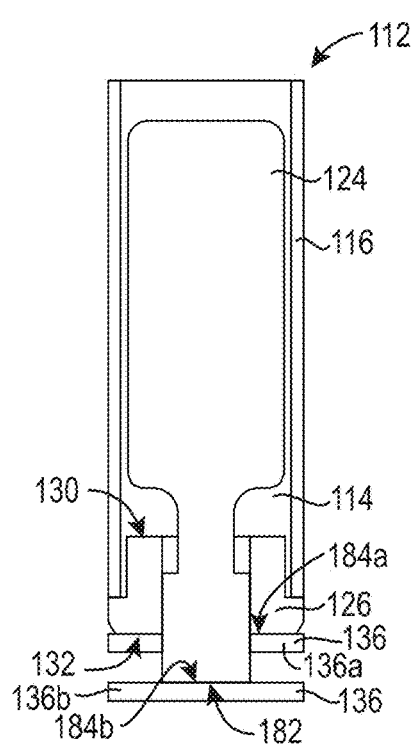
Figure 12D:
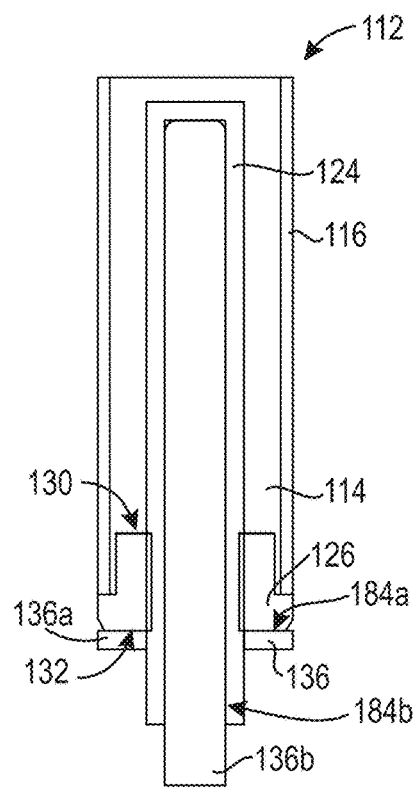

According to yet another embodiment, as shown in FIGS. 12C-12D, the porous valve element and heat transfer element are heated by separate first and second heating elements 136*a*, 136*b*. For example, according to certain embodiments, the porous valve element is configured to be heated by a first heating element 136*a* in thermal contact with the vaporizing surface of the porous valve element, and heat transfer element is heated by a second heating element 136*b* in contact with a base surface of the heat transfer element that is at a same side of the device as the vaporizing surface of the porous valve element, as shown for example in FIG. 12C. For example, the first heating element may be a donut shaped heating plate that surrounds a periphery of the base of the heat transfer element and contacts the bottom portion of the vaporizing surface with an upper surface thereof, whereas the second heating element can comprise a plate with an upper surface placed in contact with the end surface of the heat transfer element. In the embodiment as shown in FIG. 12D, a first heating element 136*a* can comprise a donut shaped plate heater as in FIG. 12C, but the second heating element 136*b* can comprise a rod heater inserted into a ceramic sheath comprising the heat transfer element. That is, according to one embodiment, the porous valve element can be heated by a first heating element in thermal contact with the vaporizing surface of the porous valve element, and the heat transfer element can be heated by a second heating element that extends along an internal length of the heat transfer element. Other configurations of heating elements and configurations of contact with the porous valve element and heat transfer element can also be provided that are other than those specifically described and/or shown herein. Furthermore, the one or more heating elements 136 can comprise a variety of different heating elements, including one or more of a rod heater, a ring heater, a disc heater, a plate heater, a coil heater, a pancake coil (see, e.g., FIG. 17), and/or the first and second heating elements are external or internal to one or more of the porous valve element and/or heat transfer element.

According to certain embodiments, the vaporizable product used in the device 100 and/or cartridge 112 can be any one or more of a liquid, a wax and/or a material that is substantially solid at room temperature. For example, the vaporizable product comprises any one or more of hash, cannabidiol, and a cannabis oil distillate.

Figure 11A:
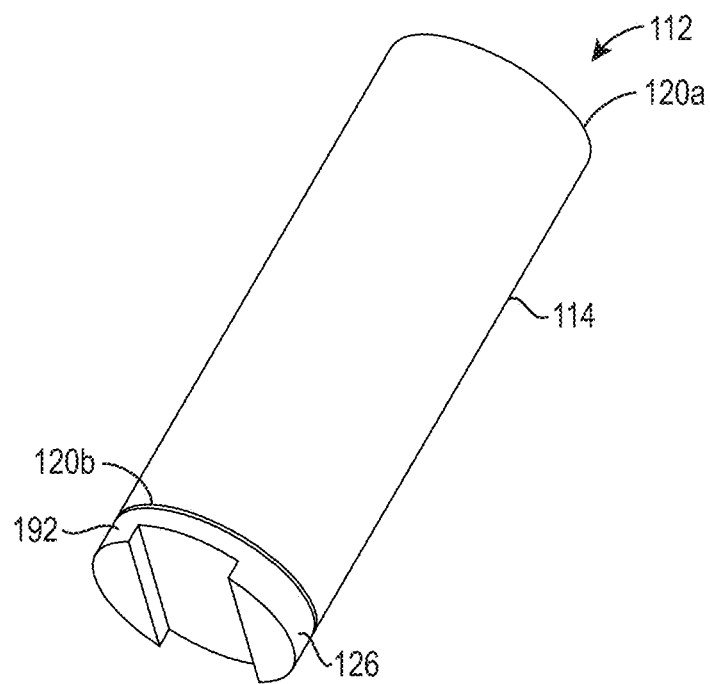
FIGS. 11A-11C depict isometric, and cross-sectional views of embodiments of cartridges according to aspects herein.
Figure 11B:
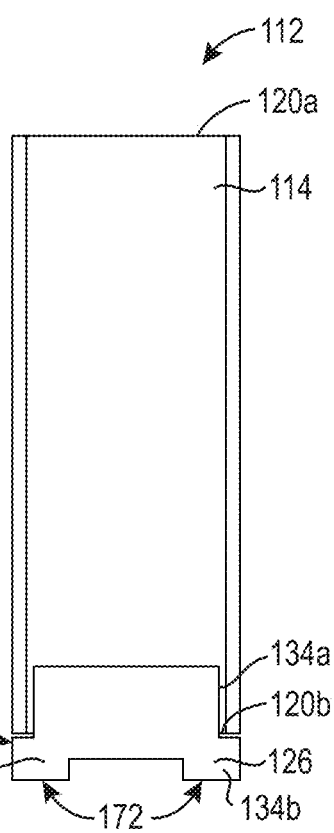
Figure 11C:
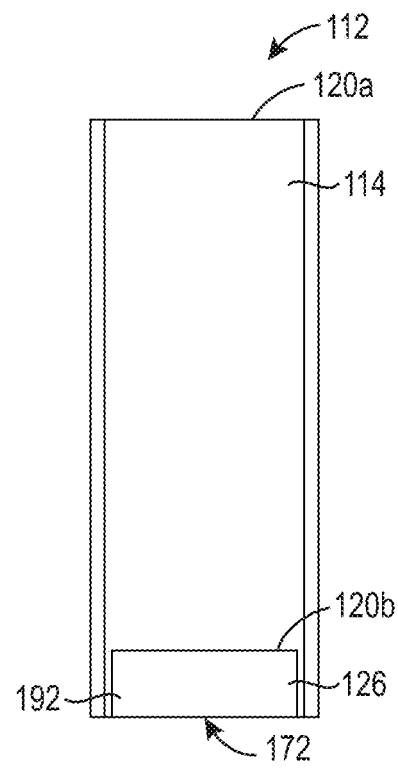

Referring to the embodiment as shown in FIGS. 11A-11B, according to certain aspects, a portable vaporizing device and/or cartridge may be provided that does not include a heat transfer element such as a heat conducting column, but instead provides heating via the porous valve element 126. For example, as shown in FIGS. 11A-11C, the porous valve element can comprise a disc-like fitting at a lower end 120*b* of the product chamber 114. Similarly to the annular fitting described with respect to FIGS. 4A-4C above, the disc-like fitting can in certain embodiments comprise upper and lower portions 134*a*, 134*b*, where the lower portion 134*b* extends beyond the walls of the chamber and can have a diameter greater than that of the upper portion, and the vaporizing surface 132 includes both a bottom portion 172 and peripheral portions 170 through which vaporized product can exit the product chamber via the porous valve element, as shown in FIG. 11B. In another embodiment, the disc-like fitting is sized to fit within the annular walls of the chamber, and comprises a bottom surface 172 that acts as the vaporizing surface 132 to pass vapor therethrough, as shown in FIG. 11C. As another embodiment, the disc-like fitting may serve as a stopper to close the bottom opening of the product chamber. The disc-like fitting may also comprise grooves and/or channels 150 formed in the vaporizing surface thereof, to promote the passage of vaporized product away from the vaporizing surface, as discussed elsewhere herein for other embodiments of the porous valve element.

Referring to FIGS. 11A-11C, according to one embodiment of a portable vaporizing device and/or cartridge that uses the porous valve element as the source of heating of the vaporizable product (e.g., without a heat transfer element), the device and/or cartridge comprises the vaporizable product receiving chamber 114 configured to receive the vaporizable product therein, the vaporizable product receiving chamber comprising one or more chamber walls 122 defining a product flow path between upper and lower opposing ends of the vaporizable product receiving chamber, and the porous valve element 126 located towards the lower end 120b of the vaporizable product receiving chamber that is configured to heat the vaporizable product to the predetermined viscosity. The porous valve element can comprise the porous valve body comprising porous material configured to allow heated vaporizable product having the predetermined viscosity to pass therethrough.

According to certain embodiments, the porous valve further comprises at least one exposed first porous entry surface of the porous valve body that is configured to be placed in direct thermal contact with vaporizable product in the product chamber to transfer heat thereto. The at least one first porous entry surface is configured to receive the heated vaporizable product from the product flow path into the porous valve body. In one embodiment, the exposed first porous entry surface comprising a porous material having a thermal conductivity of at least 0.5 W/m*K to allow for adequate heating of the exposed first porous entry surface 130 and heating of the product in thermal contact with the exposed first porous entry surface 130. As similarly discussed above, by "exposed" surface it is meant that the first porous entry surface is in direct contact with the vaporizable product in the chamber, without any intervening layers, such that the product enters the entry surface 130 directly upon heating to the predetermined temperature, without passing through any other filtering or cover materials. That is, the first porous entry surface is uncovered and is in direct contact with the vaporizable product in the product chamber.

According to certain embodiments, the at least one porous vaporizing surface is configured to flow the heated vaporizable product therethrough such that the vaporizable product is at least partially vaporized in the vicinity of the at least one porous vaporizing surface while exiting the porous valve body. Furthermore, referring to FIGS. 11A-11C, a portion (e.g., the bottom portion 172) of the at least one porous vaporizing surface is on a side of the porous valve body opposite the first porous entry surface, and the portion of the at least one porous vaporizing surface is configured to be placed into direct contact with at least one heating element to provide heating of the porous valve element during operation of the portable vaporizing device.

The portable vaporizing device and/or cartridge having the product chamber and porous valve element 126 (e.g., without the heat transfer element 124) can comprise any of the other features, characteristics, parameters and/or structures otherwise described herein, such as any described herein with respect to FIGS. 1A-10 and 12A-14B. For example, in one embodiment, the bottom portion of the vaporizing surface of the porous valve element may be placed in a compressed relationship with at least one heating element, such as a heating plate and/or heating ring. As another example, the porous valve element may also be capable of being heated to any of the temperatures and/or at the heating rates described elsewhere herein as being obtainable therewith, and/or to achieve the predetermined viscosities described elsewhere herein. As yet another example, the porous valve element can comprise any of the materials or properties described elsewhere herein, such as for example a porous borosilicate material.

Figure 13A:
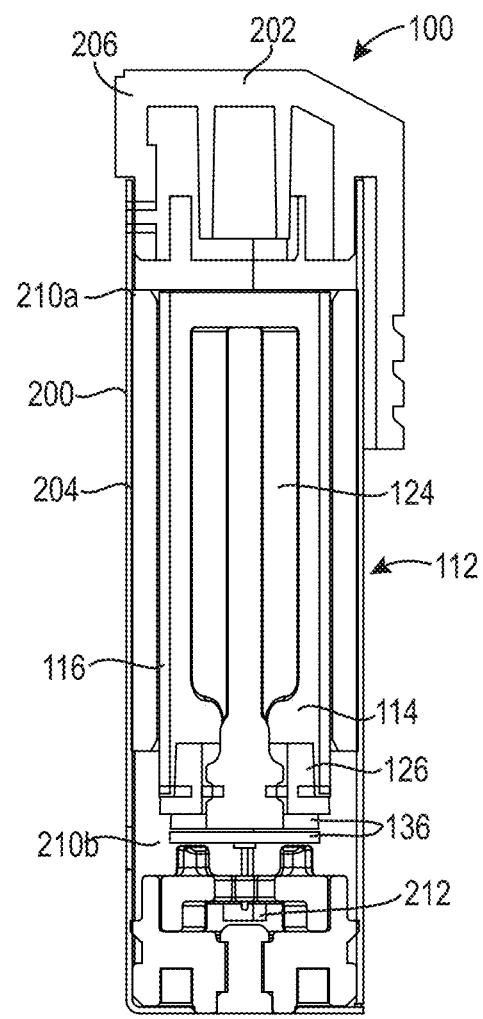
FIGS. 13A-13B are sectional views of a vaporizing device suitable for use with a cartridge according to aspects herein.
Figure 13B:
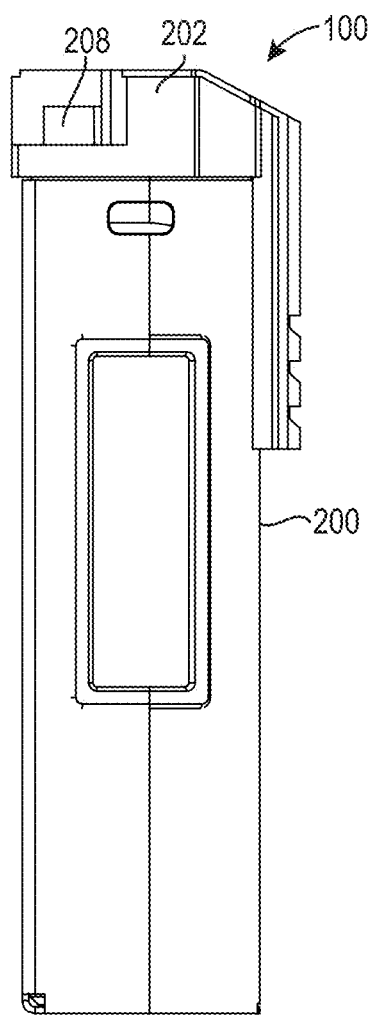
Figure 15:
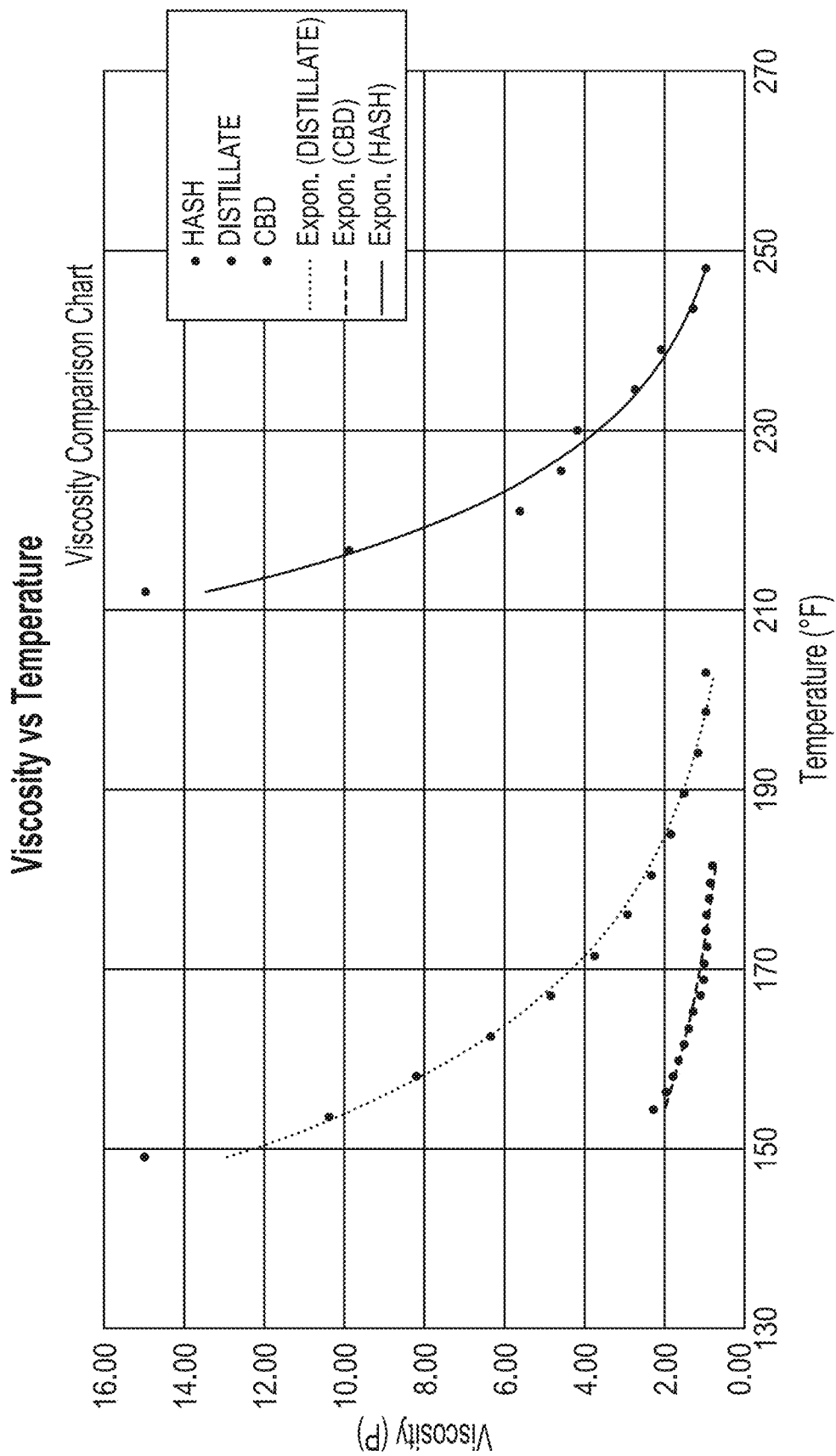
FIG. 15 is a graph showing change in viscosity for increasing temperature for hash, distillate and cannabidiol.
Figure 16:
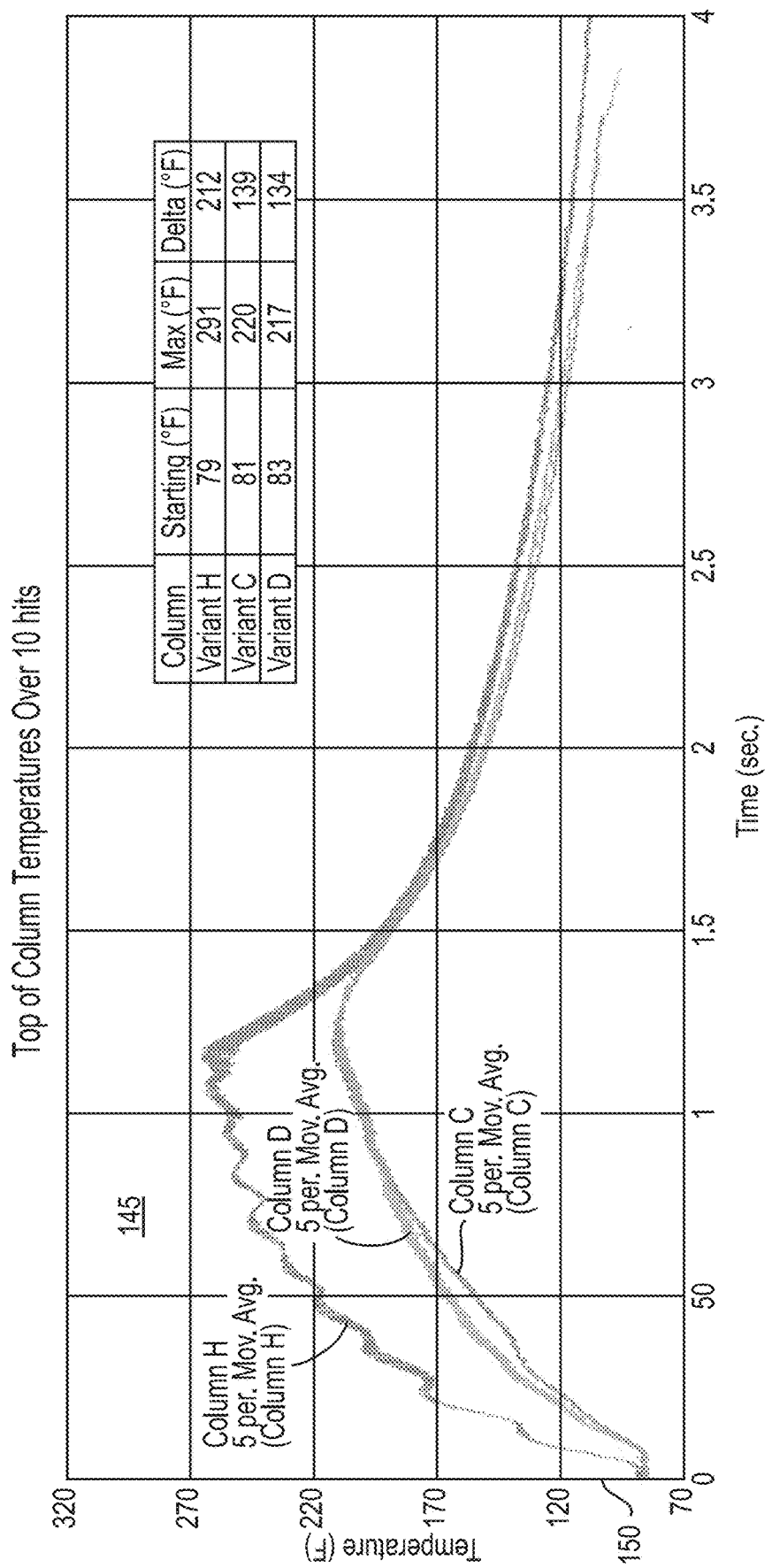
FIG. 16 is a graph showing temperature over time for heating in different embodiments of cartridges according to aspects herein.
Figure 18:
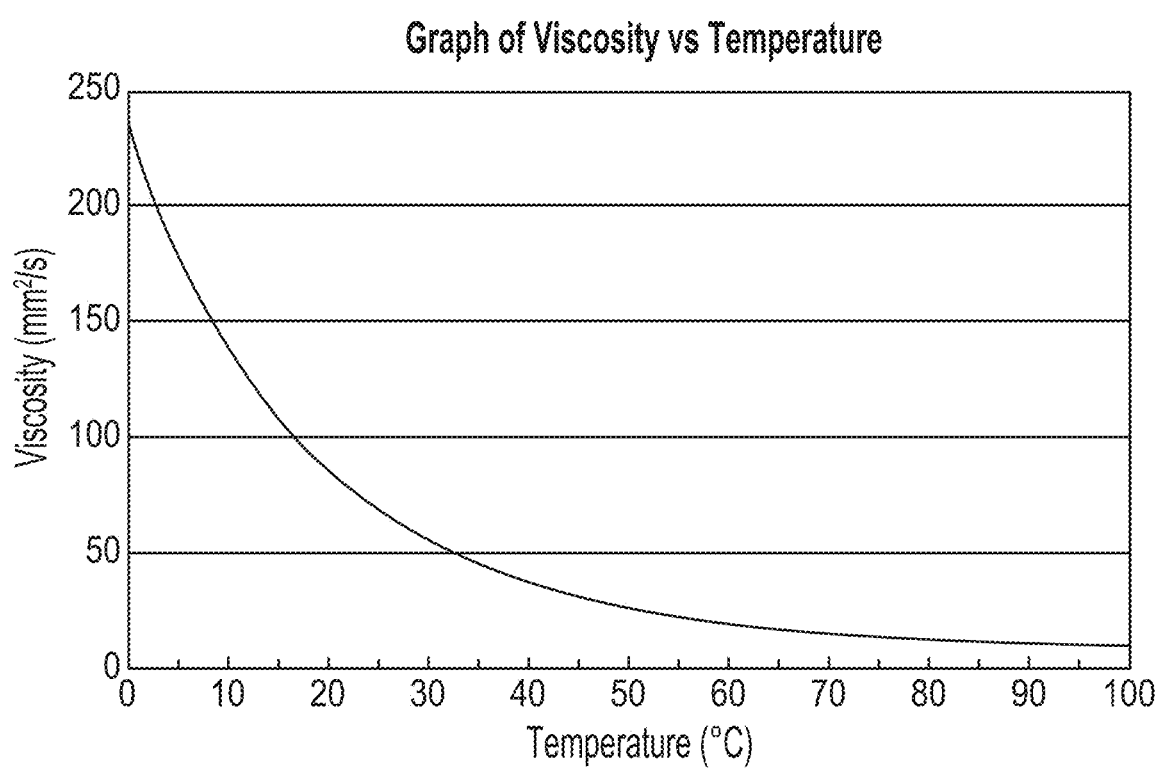
FIG. 18 is a graphical representation of a substance's viscosity in relation to temperature.
Figure 19:
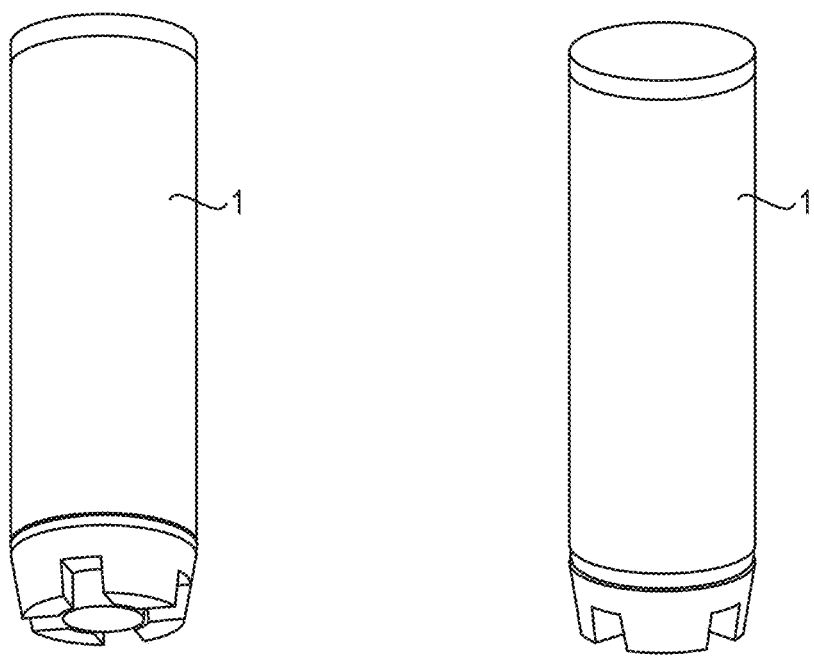
FIG. 19 is a front perspective view of the cartridge according to an embodiment of the present invention.
Figure 20:
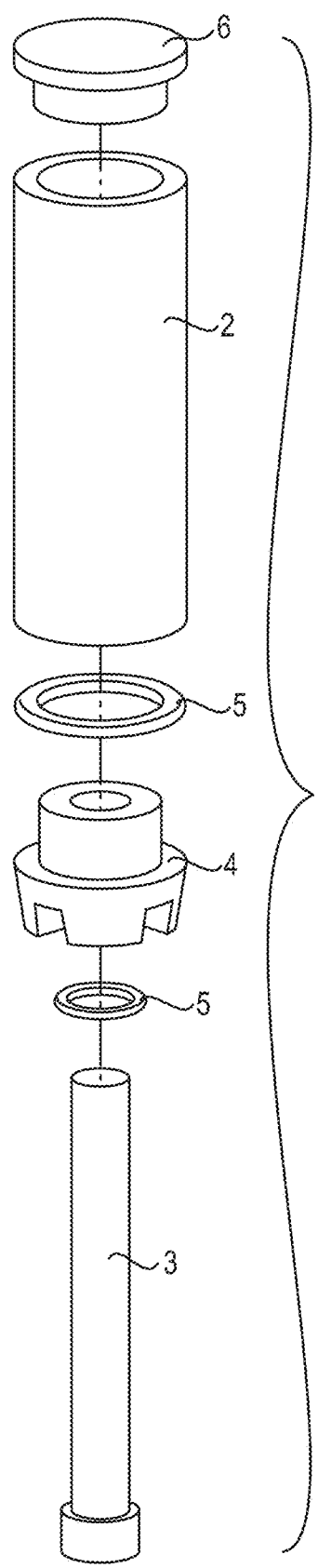
FIG. 20 is an exploded view of the cartridge according to an embodiment of the present invention.
Figure 21:
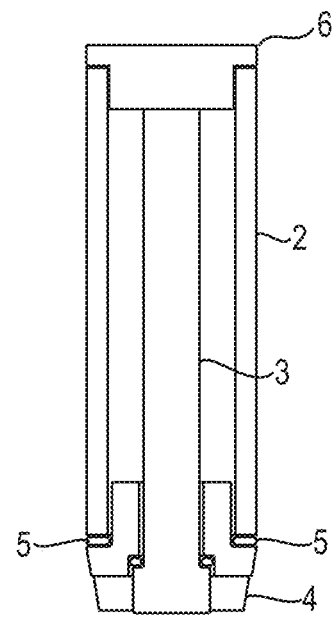
FIG. 21 is a schematic view of the cartridge according to an embodiment of the present invention.
Figure 22:
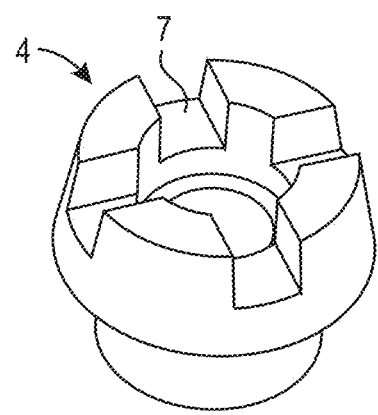
FIG. 22 shows an embodiment of wick and grooves.
Figure 23:
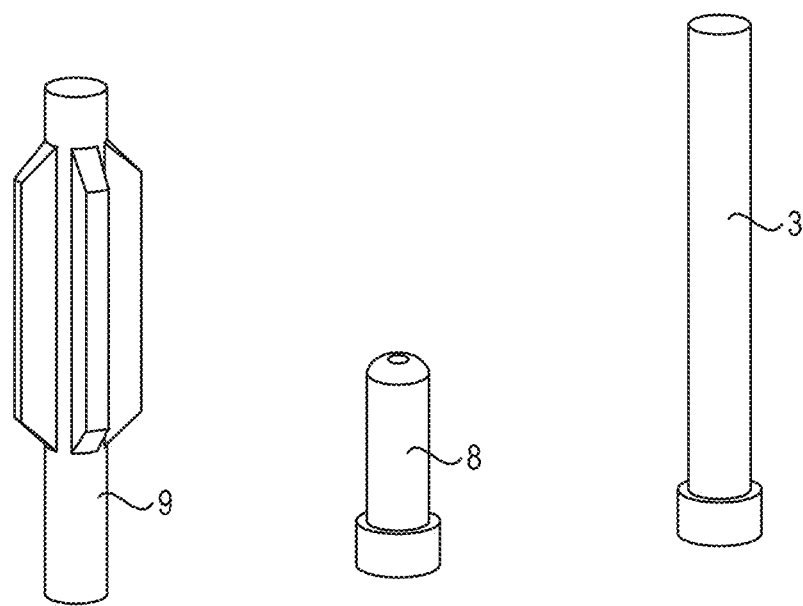
FIG. 23 shows a perspective view of embodiments of the center column.
Figure 24:
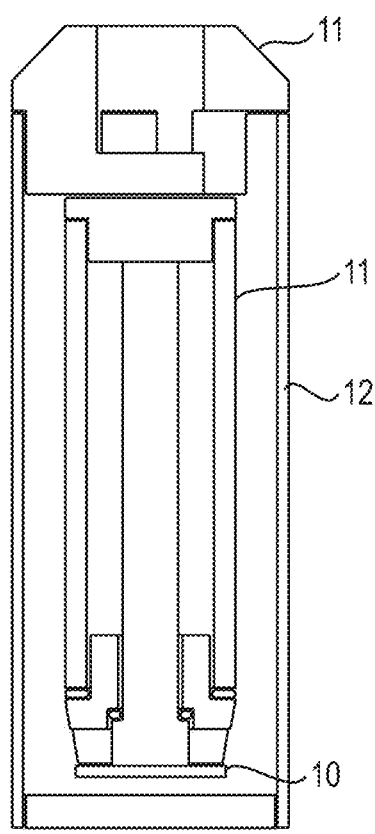
FIG. 24 is a schematic view of an embodiment of the invention showing the mouthpiece, heating element, and cartridge.
Figure 25A:
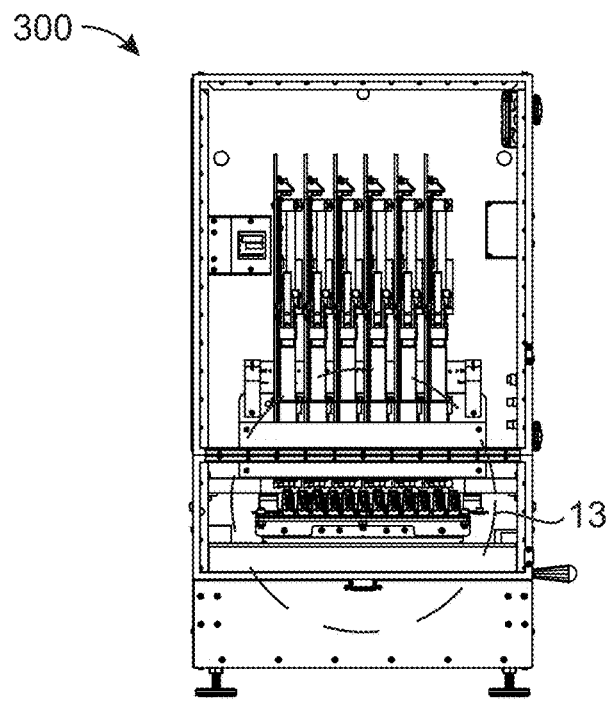
FIGS. 25A-25F are various views of an embodiment of an automated filling system according to aspects herein.
Figure 25B:
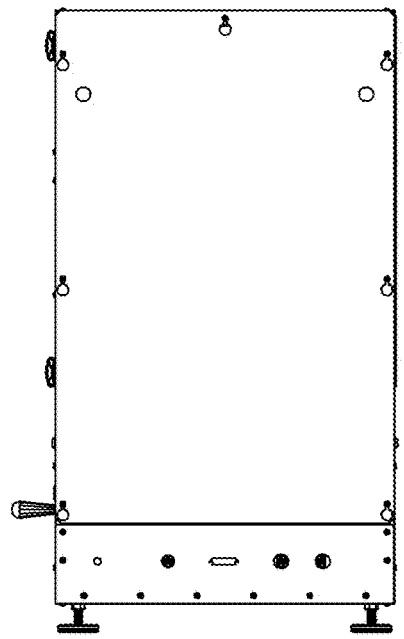
Figure 25C:
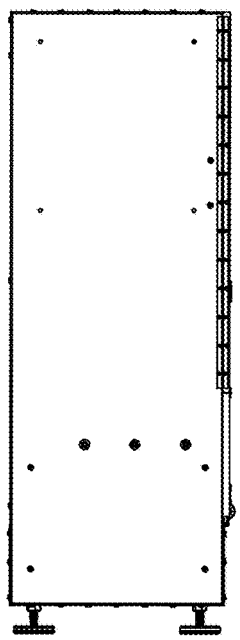
Figure 25D:
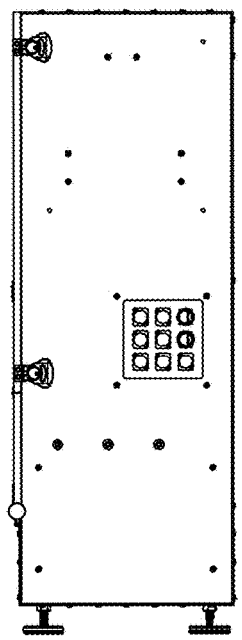
Figure 25E:
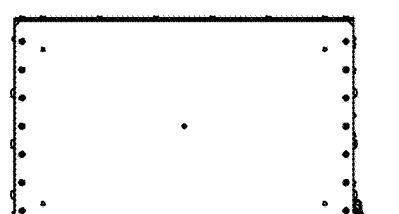
Figure 25F:
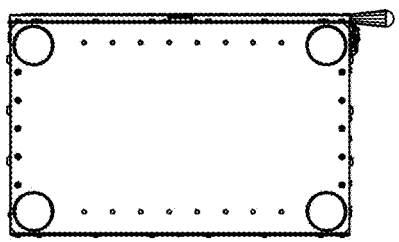

Referring to FIGS. 13A-13B and 14A-14B, embodiments of a portable vaporizing device 100 comprising the product chamber 114 and porous valve element 126, and optionally with the heat transfer element 124, is described. For example, the portable vaporizing device 100 may be configured to receive a removable single-use or refillable cartridge 112 comprising the product chamber 114 and porous valve element 126, with optional heat transfer element, such as any of those disclosed herein. Referring to FIG. 13A, in one embodiment, the device comprises a housing 200 that is configured to accommodate the product chamber and porous valve element (and optionally heat transfer element) therein. For example, the housing 200 can be configured to accommodate a cartridge 112 therein, with an openable cap 202 portion that can be opened or closed to refill the housing with fresh cartridges.

According to one embodiment, the portable vaporizing device further comprises a gas flow chamber 204 configured to receive vaporized product exiting the product chamber 114 via the porous valve element 126, and direct the vaporized product towards a mouthpiece 206 (e.g., in the cap 202) comprising an inhalation outlet 208 that allows for inhalation of the vaporized product. In one embodiment, the gas flow chamber 204 is external to the product chamber 114, and re-directs a flow of vaporized product from a bottom end 210b of the gas flow chamber 204 where product is received from the vaporizing surface of the porous valve element, to a top end 210a of the gas flow chamber 204 to flow the vaporized product to the mouthpiece 206. In one embodiment, the gas flow chamber 204 is external to and laterally surrounds the product chamber 114. For example, the gas flow chamber 204 may be at least partly defined by the space in between the sidewalls 212 of the housing, and the product chamber sidewalls 122, to form a conduit therebetween for the passage of vaporized product. In one embodiment, the gas flow chamber 204 is configured to receive vaporized product exiting the porous valve element in a lateral direction, and re-direct the flow of vaporized product upwardly and external to the product chamber to the mouthpiece.

In certain embodiments, the portable vaporizing device may also comprise a power source 212, such as a battery configured to provide power to the heating element(s) 136 to cause the heating element(s) to heat during operation of the device. In one embodiment, operation of the device, such as by pushing a switch, causes power to be delivered to the heating elements during a heating cycle, which may for example by about 10 seconds, to vaporize the product. According to yet another embodiment, the device 100 comprises one or more heating elements that may be permanently or semi-permanently affixed therein, and where the device is configured to receive a cartridge such that the surfaces of the porous valve element and/or heat transfer element that are to be heated are placed in direct physical contact with the one or more heating elements. The device may also be capable of providing the heating elements in compressed relation with respect to the porous valve element and/or heat transfer element, such that a close fit can be provided.

Filling System and Method

Other aspects of the invention as described herein are directed to methods and/or automated systems for filling a cartridge 112 used in a portable vaporizing device 100 with a vaporizable product as described herein. According to certain embodiments, the one or more internal heat-conducting surfaces can be used to at least partially heat the vaporizable product during the filling process, such as to increase the flowability and reduce the viscosity of vaporizable product as it is being provided to the cartridge receiving chamber. In some embodiments, the cartridge comprises one or more chamber walls 116 defining a product flow path 118 between the upper and lower opposing ends 120a, 120b of the vaporizable product receiving chamber 114, and wherein the one or more internal heat-conducting surfaces comprise at least one interior surface 119 of the one or more chamber walls 116, the method comprising heating the at least one interior surface 119 of the chamber walls, and introducing the vaporizable product into the upper end 120a of the vaporizable product receiving chamber, such that the vaporizable product flows along the one or more heated interior surface(s) of the chamber walls toward the lower end 120b of the vaporizable product receiving chamber. In some embodiments, the cartridge comprises an elongate heat-conducting column 154 within the vaporizable product receiving chamber and extending in between the upper and lower opposing ends therein, and wherein the one or more internal heat-conducting surfaces include at least one surface 140 of the elongate heat-conducting column 154, and wherein the method comprising heating the elongate heat-conducting column 154, and introducing the vaporizable product into the upper end 120a of the vaporizable product receiving chamber 114, such that the vaporizable product flows along the at least one heated surface 140 of the elongate heat-conducting column toward the lower end 120b of the vaporizable product receiving chamber. In some embodiments, the one or more internal heat-conducting surfaces may further include at least one surface 127 of a porous valve element 126. In some embodiments, the one or more internal heat-conducting surfaces may be heated to temperatures that are lower than a temperature used for normal operation of the portable vaporizing device, to provide improved performance in filling of the cartridge with the vaporizable product.

Accordingly, in one embodiment of the invention, a method for filling the cartridge 112 used in the portable vaporizing device 100 with a vaporizable product is provided. As described elsewhere herein, the cartridge 112 comprises the vaporizable product receiving chamber 114 configured to receive a vaporizable product therein, and having upper and lower opposing ends 120a, 120b, one or more internal heat-conducting surfaces comprising surfaces of an elongate heat-conducting column 154 within the vaporizable product receiving chamber and extending in between the upper and lower opposing ends thereof, and/or surfaces of internal walls of the product receiving chamber 119, and the porous valve element 126 the porous valve element being configured to at least partially vaporize the vaporizable product as it exits the vaporizable product receiving chamber by passing therethrough.

According to certain embodiments, the method of filling comprises heating the one or more internal heat-conducting surfaces, and introducing the vaporizable product into the upper end 120a of the vaporizable product receiving chamber 114 to at least partly fill the chamber. The vaporizable product introduced into the upper end 120a of the vaporizable product receiving chamber flows along the heated one or more internal heat-conducting surfaces, e.g. via force of gravity, towards the lower end 120b of the vaporizable product receiving chamber. That is, according to certain embodiments, the one or more internal heat-conducting surfaces serves to heat the vaporizable product as it flows into and/or through the receiving chamber during the filling process. The heated vaporizable product that is heated by the one or more internal heat-conducting surfaces may have improved flowability into the vaporizable product receiving chamber, to enhance the filling process, such as by reducing the viscosity of the vaporizable product. Any clogging and/or impeding of the flow of vaporizable product into the product receiving chamber can also be reduced by heating of the one or more internal heat-conducting surfaces, by improving the flowability of the vaporizable product. In certain embodiments, the vaporizable product may also be optionally pre-heated prior to introducing into product receiving chamber 114, such as to further improve flowability of the product. For example, in one embodiment, the vaporizable product is pre-heated to a temperature of at least 80° C., at least 90° C., at least 100° C. and/or at least 110 ° C., prior to introduction into the product receiving chamber. However, in alternative embodiments, the vaporizable product is not pre-heated prior to introduction into the product receiving chamber 114. In some embodiments, the one or more internal heat-conducting surfaces is heated by a heating element 203, which may be provided either separately or as a part of the cartridge and/or portable vaporizing device 100. For example, the heating element 203 may be any of those discussed as suitable for use with the portable vaporizing device and/or cartridge elsewhere herein. The heating element 203 may comprise, for example, one or more of a rod heater, a ring heater, a disc heater, a plate heater, a coil heater, and pancake coil. In some embodiments, the one or more internal heat-conducting surfaces are surfaces of the elongate heat-conducting column 154, and the elongate heat-conducting column is heated by contacting the base surface of the elongate heat-conducting column with a heating plate, as described elsewhere herein. In some embodiments, the one or more internal heat-conducting surfaces are at least one interior surface 119 of the chamber walls 116, and the at least one interior surface of the chamber walls is heated by contacting outer surfaces of the chambers walls of the cartridge with a heating element as described elsewhere herein.

According to certain embodiments, the one or more internal heat-conducting surfaces may be heated simultaneously with, immediately prior to, and/or immediately after, initiation of introduction of the vaporizable product into the vaporizable product receiving chamber. In some embodiments, the one or more internal heat-conducting surfaces are pre-heated prior to introduction of the vaporizable product into the vaporizable product receiving chamber. For example, the one or more internal heat-conducting surfaces may be pre-heated to reach a predetermined temperature of the one or more internal heat-conducting surfaces that facilitates flow of the vaporizable product, prior to introduction of the vaporizable product into the product receiving chamber. In one embodiment, the one or more internal heat-conducting surfaces are pre-heated prior to introduction of the vaporizable product into the product receiving chamber, and heating of the one or more internal heat-conducting surfaces is maintained during at least a portion, and even the entire, filling process, until a predetermined volume of the vaporizable product has been provided to the product receiving chamber. In yet another embodiment, the one or more internal heat-conducting surfaces are pre-heated prior to introduction of the vaporizable product into the product receiving chamber, and heating of the one or more internal heat-conducting surfaces is allowed to cease at a point during filling of the product receiving chamber, such as in a case where the residual heat provided by the one or more internal heat-conducting surfaces is sufficient to improve flowability of the vaporizable product.

According to yet another embodiment, heating of the one or more internal heat-conducting surfaces is initiated substantially simultaneously with introduction of the vaporizable product into the product receiving chamber (e.g. without pre-heating of the one or more internal heat-conducting surfaces). According to yet a further embodiment, heating of the one or more internal heat-conducting surfaces is initiated shortly after introduction of the vaporizable product into the product receiving chamber, such as for example to improve flow of the vaporizable product to the lower end of the product receiving chamber.

According one embodiment, heating of the one or more internal heat-conducting surfaces is maintained during at least a portion of the duration of time in which the vaporizable product receiving chamber is being filled with the vaporizable product, such as until a predetermined volume of the vaporizable product has been received in the vaporizable product receiving chamber. In another embodiment, heating of the one or more internal heat-conducting surfaces is maintained during an entirety of a duration of time in which the vaporizable product receiving chamber is being filled, such as until a predetermined volume of the vaporizable product has been received in the vaporizable product receiving chamber. In one embodiment, heating of the one or more internal heat-conducting surfaces may be maintained during at least a portion of the filling process, with different temperatures of the one or more internal heat-conducting surfaces being provided at different stages of the filling process. In yet another embodiment, the temperature of the one or more internal heat-conducting surfaces may be maintained at substantially the same temperature throughout a major portion, and even the entire, filling process, until a predetermined volume of the vaporizable product has been provided to the product receiving chamber. The predetermined volume may correspond to a finished fill volume of the cartridge, such as a volume that substantially fills the product receiving chamber (e.g. at least 75%, at least 80%, at least 90%, at least 95% and/or at least 99% of the internal volume of the product receiving chamber), and/or that fills it to an extent that renders the cartridge suitable for use by a user.

According to yet further embodiments, the porous valve element 126 may be heated, to facilitate filling of the product receiving chamber 114. For example, the porous valve element 126 can, in certain embodiments, be heated simultaneously with heating of one or more other internal heat-conducting surfaces, such as the elongate heat-conducting column, such as by placing both in thermal contact with the same heating plate. In other embodiments, the porous valve element 126 can be heated separately from other internal heat-conducting surfaces, such as by a separate heating element. In further embodiments, the porous valve element 126 may be heated before or after heating of one or more other internal heat-conducting surfaces. For example, the porous valve element 126 can, in certain embodiments, be heated at a predetermined point in time after heating of the one or more other internal heat-conducting surfaces has ceased, to facilitate flow of the vaporizable product that has been received in the product receiving chamber into the porous valve element and/or to saturate the porous valve element with the vaporizable product. The porous valve element can also be heated to a same or different temperature than one or more other internal heat-conducting surfaces, according to desired filling parameters. In some embodiments, the porous valve element is heated by a same or different heating element as one or more other internal heat-conducting surfaces, during at least a portion of a duration of time in which the vaporizable product receiving chamber is being filled with the vaporizable product, such as to the predetermined fill volume. In certain embodiments, the porous valve element is heated simultaneously with, immediately prior to, or immediately after, initiation of introduction of the vaporizable product into the vaporizable product receiving chamber. In certain embodiments, the porous valve element may be continuously heated throughout the filling process, and/or heating of the porous valve element may be initiated after the product receiving chamber has been at least partly filled with the vaporizable product, such as to facilitate saturation of the porous valve element with the vaporizable product. In one embodiment, heating of the porous valve element may be maintained during at least a portion of the filling process, with different temperatures of the porous valve element being provided at different stages of the filling process. In yet another embodiment, the temperature of the porous valve element may be maintained at substantially the same temperature throughout a portion, and even the entire, filling process, such as until a predetermined volume of the vaporizable product has been provided to the product receiving chamber.

In some embodiments, the one or more internal heat-conducting surfaces are heated to a temperature that is lower than an operational temperature of the respective one or more internal heat-conducting surfaces, that used for vaporization of the vaporizable product from the cartridge and inhalation thereof by a user. For example, in certain embodiments, the one or more internal heat-conducting surfaces, such as the elongate heat-conducting column are heated to a temperature that is at least 20%, at least 25%, at least 30%, and/or at least 50% lower than the operational temperature of the one or more internal heat-conducting surfaces used for vaporization of the vaporizable product from the cartridge and inhalation thereof by the user. Generally, an operational temperature in the normal use cycle ("hit") for the one or more internal heating-surfaces, such as the elongate heat-conducting column and porous valve element, is measured at the end of a single hit, which starts at room temperature and runs for 8 seconds, with the measurement taken at the end of 8 seconds. The values can be measured for several cartridges, and averaged over at least 3, at least 4, at least 5, and/or even at least 10 cartridges. In one embodiment, the average operational temperature in the normal use cycle for the elongate heat-conducting column would be greater than 75° C., such as at least 80° C. In some embodiments, during the filling process, the elongate heat-conducting column is heated to a temperature that is at least 10° C. less, at least 15° C. less, or even at least 20° C. less than the average operational temperature of the elongate heat-conducting column. As another example, in certain embodiments, the porous valve element is heated to a temperature that is at least 20%, at least 25%, at least 30%, and/or at least 50% lower than the operational temperature of the porous valve element used for vaporization of the vaporizable product from the cartridge and inhalation thereof by the user. In one embodiment, the average operational temperature in the normal use cycle for the porous valve element would be greater than 90° C., such as at least 100° C. or even at least 110° C. In some embodiments, during the filling process, the porous valve element is heated to a temperature that is at least 10° C. less, at least 15° C. less, at least 20° C. less, or even at least 25° C. less than the average operational temperature of the porous valve element. The lower heating temperature may help preserve and reduce deterioration of the vaporizable product provided in the receiving chamber. In one embodiment, the operational temperature is a minimum temperature required to at least partially vaporize the vaporizable product during operation of the portable vaporizing device comprising the cartridge, for inhalation by a user. For example, in one embodiment, the one or more internal heat-conducting surfaces, such as the elongate heat-conducting column may be heated to a temperature of no more than 75° C., such as no more than 70° C., and even no more than 65° C. In another embodiment, the elongate heat-conducting column may be heated to a temperature of at least 45° C., at least 50° C., at least 55° C. and/or at least 60° C. In one embodiment, the porous valve element may be heated to a temperature of no more than 90° C., such as no more than 85° C., no more than 80° C., and/or even no more than 75° C. In another embodiment, the porous valve element may be heated to a temperature of at least 50° C., at least 55° C., at least 60° C., at least 65° C., and/or at least 70° C.

Figure 34:
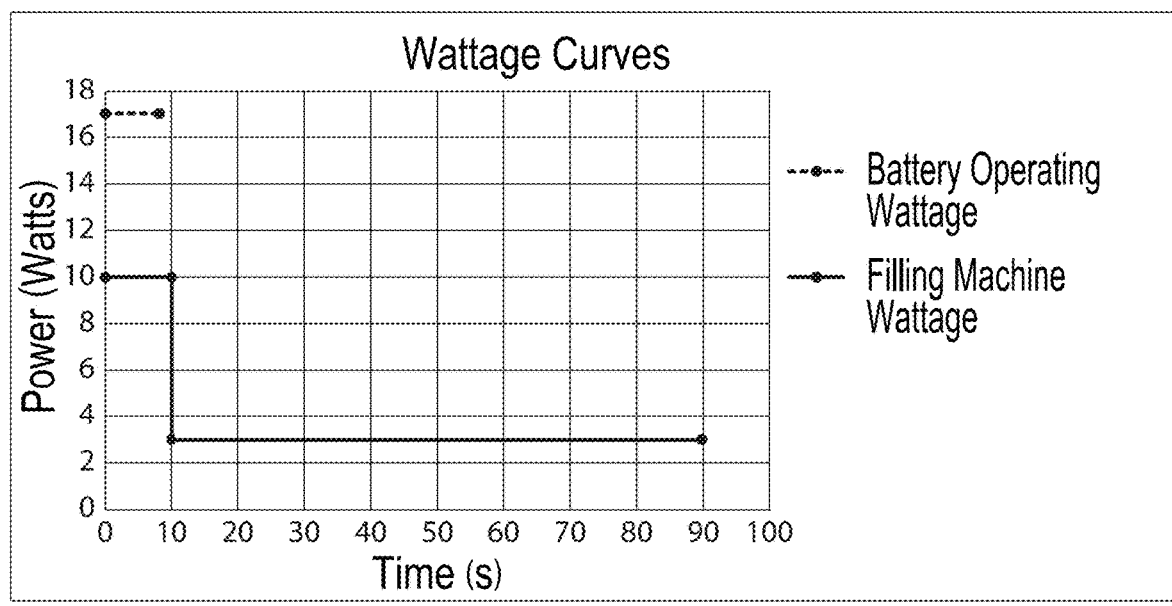
FIG. 34 shows a wattage curve for the power supplied to the cartridge during filling process, as compared to the wattage supplied to the cartridge for vaporization n of a vaporizable product during ordinary use of the cartridge in a portable vaporizing device by a consumer, according to an embodiment of the present disclosure.

In some embodiments, a wattage applied to a heating element(s) to heat the one or more internal heat-conducting surfaces, such as the elongate heat-conducting column and/or porous valve element before, after, or simultaneously with, introduction of the vaporizable product, is lower than an operational wattage thereof used for vaporization of the vaporizable product from the cartridge and inhalation thereof by a user. For example, in one embodiment, the wattage applied to the heating element(s) to heat the one or more internal heat-conducting surfaces, such as the elongate heat-conducting column and/or porous valve element is at least 20%, at least 25%, at least 30%, and/or at least 50% lower than the operational wattage thereof used for vaporization of the vaporizable product from the cartridge and inhalation thereof by the user. In one embodiment, the operational wattage is a minimum wattage required to at least partially vaporize the vaporizable product during operation of the portable vaporizing device comprising the cartridge, for inhalation by a user. For example, in one embodiment, the wattage applied to the heating element(s) to heat the one or more internal heat-conducting surfaces such as the elongate heat-conducting column and/or porous valve element may be no more than 17 W, such as no more than 15 W, and even no more than 12 W. In one embodiment, the wattage applied to the heating element(s) to heat the one or more internal heat-conducting surfaces such as the elongate heat-conducting column and/or porous valve element is at least 2W, such as at least 3 W, such as at least 5 W, and even at least 10 W. According to certain embodiments, an operational wattage applied to the heating element(s) to heat the one or more internal heat-conducting surfaces such as the elongate heat-conducting column and/or porous valve element may be less than 30 W, such as less than 20 W, and even less than 18 W. For example, in one embodiment, referring to FIG. 34, in one embodiment, an operational wattage of 17 W is applied to the heating element(s), such as a heating plate used to heat both the elongate heat-conducting column and porous valve element, for a duration of about 8 seconds, to provide a hit of vaporized product. In contrast, as also shown in FIG. 34, a wattage applied during a filling process comprises an initial higher wattage of about 10 W (e.g., applied to a heating plate used to heat both the elongate heat-conducting column and porous valve element) for about 10 seconds, followed by a second lower wattage of about 3 W for 80 seconds, to provide for fill of the device with the vaporizable product. According to this embodiment, both the initial and second wattages used during the filling process are lower than the wattage applied during operation of the device.

In one embodiment, the wattage applied to the heating element(s) to heat the one or more internal heat-conducting surfaces such as the elongate heat-conducting column and/or porous valve element can be varied according to different stages of the filling process. For example, in the embodiment as shown in FIG. 34, a first wattage can be applied to the heating element at the onset of heating of the elongate heat-conducting element (and/or porous valve element), and a second wattage that is lower than the first wattage can be applied to the heating element at a later point in time. For example, the first wattage can be applied to provide rapid heat-up of the one or more internal heat-conducting surfaces, such as the elongate heat-conducting column and/or porous valve element, whereas the second wattage that is lower than the first can be provided to maintain a relatively steady temperature of the one or more internal heat-conducting surfaces such as the elongate heat-conducting column and/or porous valve element during the filling process. In an example of a filling process, the initial higher wattage (e.g., 10 W) is applied during a pre-heating stage, to quickly preheat the one or more internal heat-conducting surfaces, such as the elongate heat-conducting column and/or porous valve element, to a filling temperature with a predetermined range (e.g., 75° C.), before any vaporizable product is dispensed into the cartridge. Following this pre-heating stage, the vaporizable product is dispensed into the cartridge (e.g. by syringe) during the later lower wattage stage (e.g., 3 W), during which the temperature of the one or more internal heat-conducting surfaces is maintained within the predetermined filling temperature range, until completion (or near completion) of the filling process (e.g., 80 seconds). As another alternative, the vaporizable product may be introduced simultaneously with or towards the end of a pre-heating stage while a higher wattage is applied, such as when the internal heat-conducting temperatures are close to or have just reached the desired filling temperatures, and dispensing of vaporizable product into the cartridge can continue during a second state where the wattage is reduced to maintain the temperature of the one or more internal heat-conducting surfaces within the desired filling temperature range. The wattage provided in both the first (e.g. pre-heating) and second stages is lower than the operational wattage provided during operation of the cartridge for inhalation of the vaporizable product by the user, as can be seen from FIG. 34.

Referring to FIGS. 25A-25F and 26-29, an automated filling system 300 can be provided to carry out at least a part and even the entirety of a method of filling the cartridge 112 described herein. In some embodiments, the cartridge 112 is supported during filling by a cartridge holder 303 configured to hold the cartridge, as is described in more detail below. Further referring to FIG. 30, in one embodiment, the cartridge holder 303 has contact electrodes 306 configured to electrically contact the heating element(s) 136 to provide an electrical current for heating, and wherein a wattage supplied to the heating element 136 by the contact electrodes 306 heats one or more internal heat-conducting surfaces that may include at least one interior surface 119 of the one or more chamber walls 116, at least one surface 140 of the elongate heat-conducting column 154 and/or at least one surface 127 of porous valve element 126. In some embodiments, a wattage supplied to heat the one or more internal heat-conducting surfaces is regulated according to a predetermined power curve. For example, as shown in FIG. 34, the wattage may be varied over the course of the filling process, according to a predetermined power curve that specifies the wattage to be applied at different points in time over the course of the filling process.

In some embodiments, the vaporizable product is introduced from a container 310 positioned over the upper end 120a of the vaporizable product receiving chamber. The container 310 may optionally be heated, such as by a heating block 311, to pre-heat the vaporizable product prior to introduction into the product receiving chamber 114. In some embodiments, the vaporizable product is injected and/or otherwise dispensed into the cartridge from a container corresponding to a syringe, although other types of containers can also be provided, such as a manifold or other reservoir containing the vaporizable product. According to one embodiment, a predetermined volume of vaporizable product is injected from the syringe into the cartridge by a linear actuator 313 that pushes a syringe plunger 314 into the top of the syringe to dispense the predetermined volume therefrom, as is described in more detail below.

According to certain embodiments, the method of filling can comprise filling a plurality of cartridges sequentially and/or simultaneously. For example, in one embodiment, a plurality of cartridges can be filled sequentially by individually heating the one or more internal heat-conducting surfaces, such as the elongate heat-conducting column and/or porous valve element of a first cartridge, and introducing the vaporizable product into the first cartridge having the heated one or more internal heat-conducting surfaces, such as the elongate heat-conducting column and/or porous valve element, followed by heating the one or more internal heat-conducting surfaces, such as the elongate heat-conducting column and/or porous valve element of a second cartridge, and introducing the vaporizable product into the second cartridge having the heated one or more internal heat-conducting surfaces, such as the elongate heat-conducting column and/or porous valve element. According to yet another embodiment, the method comprises simultaneously filling a plurality of cartridges, such as by simultaneously heating the one or more internal heat-conducting surfaces, such as the elongate heat-conducting column and/or porous valve elements of a plurality of cartridges, and introducing vaporizable product into each of the plurality of cartridges having the heated one or more internal heat-conducting surfaces, such as the elongate heat-conducting column and/or porous valve elements. A combination of sequential and simultaneous filling may also be provided. In a case where simultaneous filling of a plurality of cartridges is performed, a power curve applied to heat the one or more internal heat-conducting surfaces, such as the elongate heat-conducting column and/or porous valve element in each of the plurality of cartridges may be uniform among the plurality of cartridges, or may be regulated individually for each cartridge. For example, in the simultaneous filling of a plurality of cartridges with vaporizable products having different viscosities, a power curve applied to those cartridges being filled with a more viscous vaporizable material may be other than a power curve applied to those cartridges being filled with a less viscous material. For example, the power curve applied for filling with more viscous material may apply a higher wattage, and/or for a longer duration, than a power curve applied for filling with a less viscous material. As another embodiment, the power curve may be monitored and/or regulated in real time, such as in response to sensors or visual examination of the filling process.

Referring again to FIGS. 25A-25F and 26-30, an embodiment of an automated system 300 for filling a cartridge 112 used in a portable vaporizing device 100 with a vaporizable product. An example of a fully assembled system is shown in FIGS. 26-30. The system 300 comprises a housing 301, a heating system 302 configured to heat one or more internal heat-conducting surfaces that may include at least one interior surface 119 of the one or more chamber walls 116, at least one surface 140 of the elongate heat-conducting column 154 and/or at least one surface 127 of porous valve element 126 (see FIG. 30) by supplying a power to the heating element 136 from a power source (now shown), such as a battery or electrical outlet. The system 300 further comprises a holder 303 that is configured to hold the cartridge 112, an injection system 304 configured to inject vaporizable product into the cartridge 112, and a controller 305 configured to control the heating system 302 and injection system 304. The controller 305 is configured to control the heating system 302 to heat the one or more internal heat-conducting surfaces, and is configured to control the injection system 304 to inject the vaporizable product into the upper end 120a of the vaporizable product receiving chamber 114, such that the vaporizable product is at least partially melted and/or the viscosity of the vaporizable product is reduced as the vaporizable product flows along the heated one or more internal heat-conducting surfaces towards the lower end 120b of the vaporizable product receiving chamber 114. Optionally, in some embodiments, the heating system 302 is configured to pre-heat the vaporizable product in the injection system 304 prior to introducing into the vaporizable product receiving chamber 114.

In some embodiments, the heating system 302 comprising the heating element 136 is provided separately from the cartridge 112, although the heating element 136 may also be provided as a part of the cartridge 112 as described above. In some embodiments, the controller 305 is configured to control the heating system 302 to heat the one or more internal heat-conducting surfaces before, after, and/or simultaneously with controlling the injection system 304 to inject the vaporizable product into the vaporizable product receiving chamber 114 of the cartridge 112. The controller 305 may be further configured to control the heating system 302 to heat the one or more internal heat-conducting surfaces in accordance with any heating processes described herein.

Figure 26:
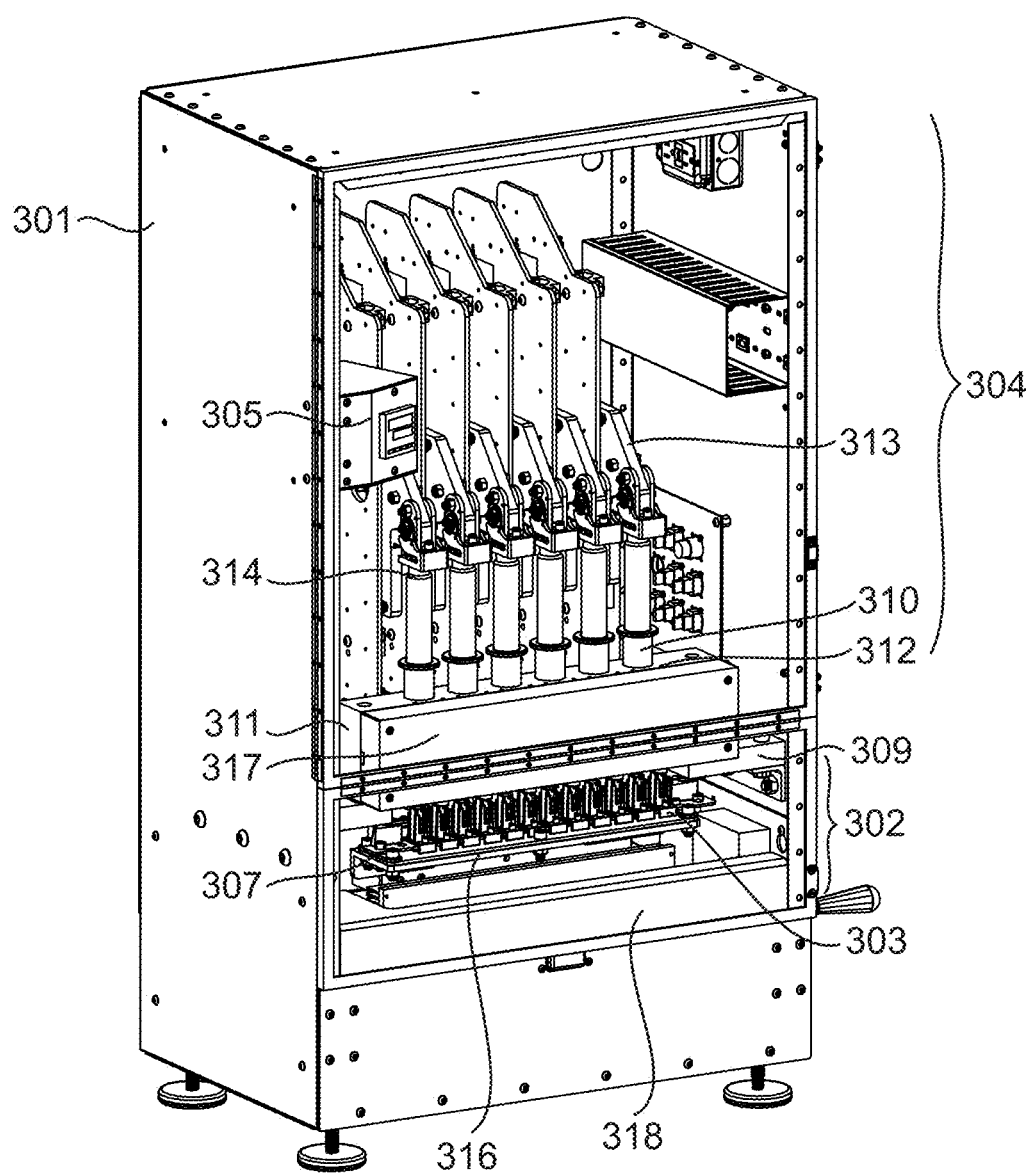
FIG. 26 is a perspective view of the automated filling system embodiment depicted in FIGS. 25A-25F.
Figure 27:
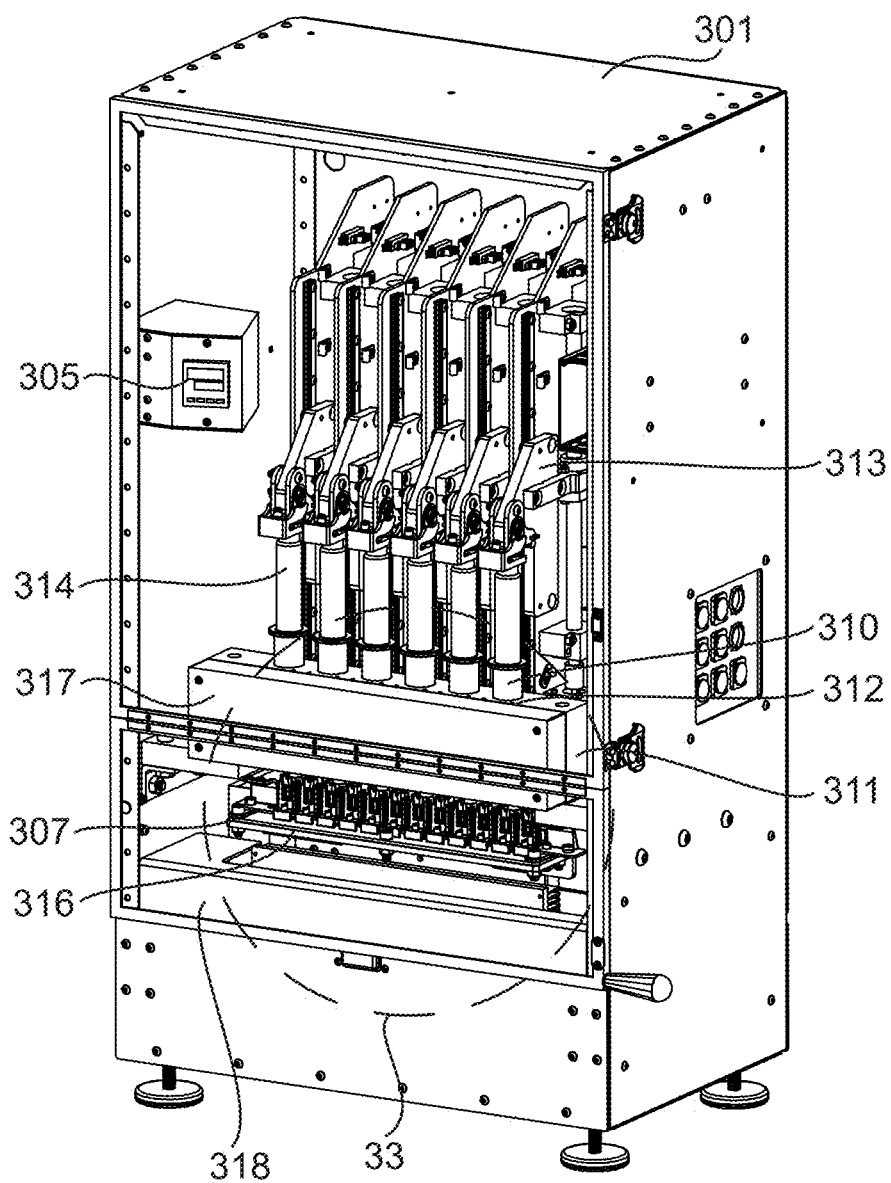
FIG. 27 is another perspective view of the automated filling system embodiment depicted in FIGS. 25A-25F.
Figure 30:
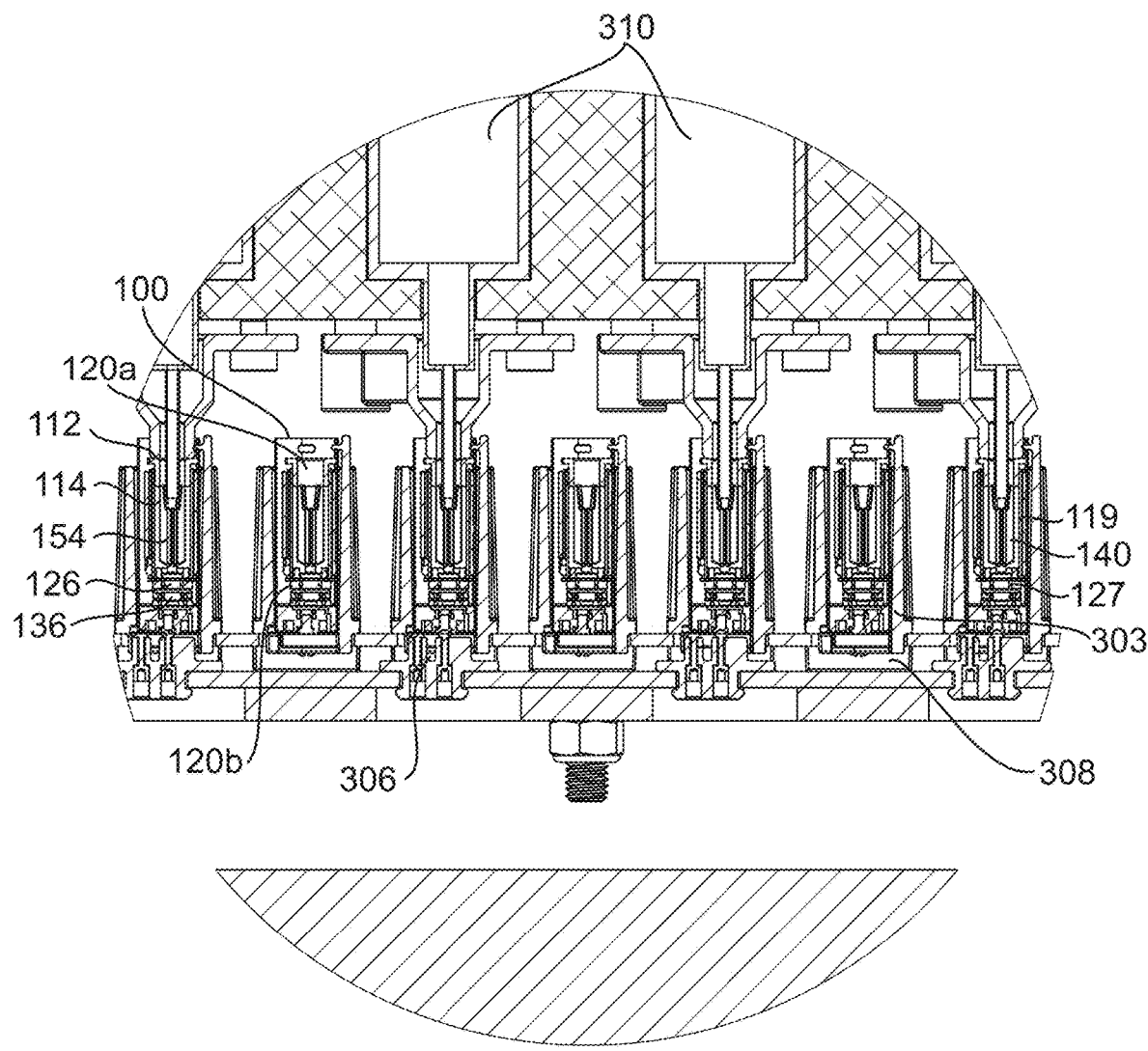
FIG. 30 is a sectional view of a section of an automated filling system according to aspects herein.

Referring to FIG. 30, in some embodiments, the cartridge holder 303 comprises contact electrode(s) 306 configured to electrically contact the heating element 136 to provide an electrical current from the power source (not shown) for heating, and a wattage supplied to the heating element 136 by the contact electrodes 306 from the power source heats e.g., the elongate heat-conducting column 154. As shown in FIGS. 26 and 30, the cartridge holder 303 comprises a filling tray 307 comprising a plurality of wells 308 configured to hold a plurality of cartridges, and wherein the plurality of wells comprise contact electrodes 306 located at a bottom of each well. Alternative embodiments for providing an electrical connection to the heating element may also be provided.

Figure 28:
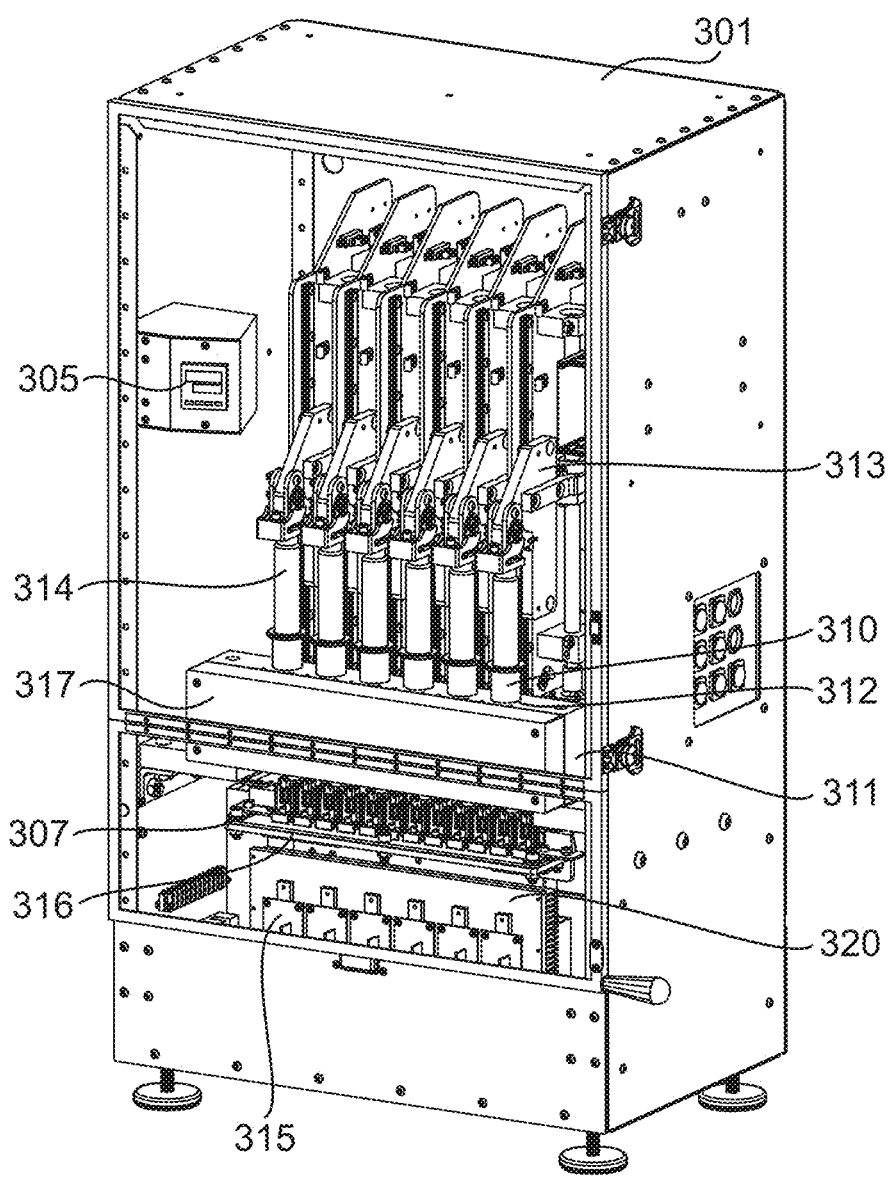
FIG. 28 is a perspective view of the automated filling system embodiment depicted in FIGS. 25A-25F with the electrical shield removed.
Figure 29:
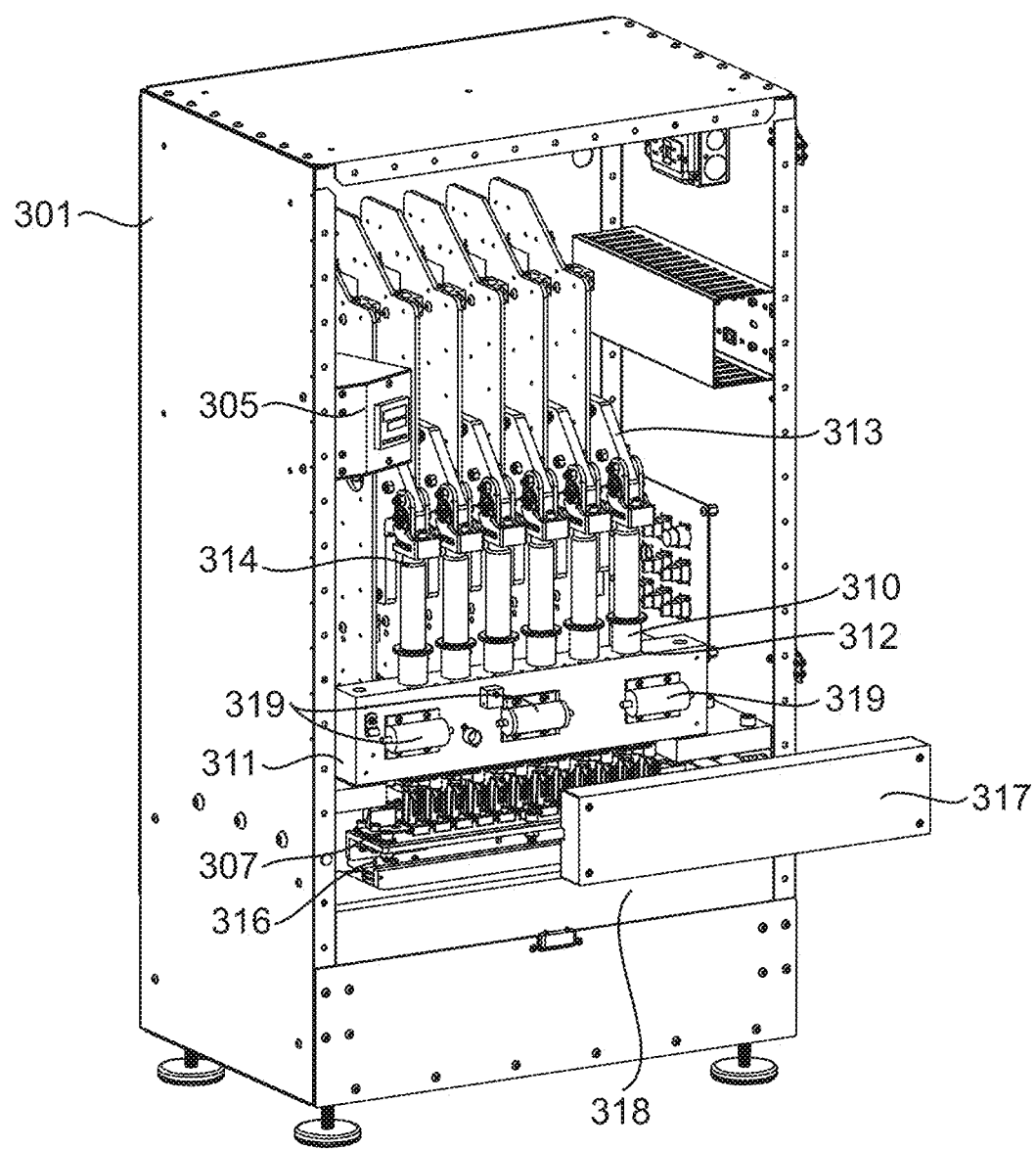
FIG. 29 is a perspective view of the automated filling system embodiment depicted in FIGS. 25A-25F with the heat block door removed.

Also as shown in FIGS. 26 and 30, in some embodiments, the injection system 304 comprises an injection container support 309 configured to support a plurality of containers 310 with vaporizable product therein at a position above or inside the upper ends 120a of a plurality of vaporizable product receiving chambers. In some embodiments, the injection system 304 comprises a heat block 311 having a plurality of holes 312 therethrough to fit a plurality of containers 310 containing the vaporizable product, and wherein the heat block 311 is heated by the heating system 302 to heat the vaporizable product held in the plurality of containers. Referring to FIG. 29, in one embodiment, the heating system 302 comprises a plurality of resistance heaters 319 to provide heat to the heat block 311. In some embodiments, the resistance heaters 319 are covered by a heat block door 317. Referring to FIGS. 26-29, in some embodiments, the injection system 304 comprises a plurality of containers corresponding to a plurality of syringes to hold the vaporizable product for injection into the cartridges. In another embodiment, the injection system 304 can comprise a container support 309 that supports a single container, such as a manifold above the cartridge, that provides vaporizable product to a plurality of cartridges, such as via a plurality of openable manifold outlets (not shown).

To drive the injection of vaporizable product into the plurality of cartridges, in one embodiment (also shown in FIGS. 26-29), the injection system 304 comprises a plurality of linear actuators 313 located above the containers (e.g. syringes) 310, which are configured to move down to physically contact ends of plungers 314 that engage a top end of the containers to push the vaporizable product through the containers and dispense into the cartridges, the linear actuators 313 being operably connected to the power source (not shown).

In some embodiments, the controller 305 is configured to independently and simultaneously control heating of a plurality of cartridges on an individual cartridge basis according to predetermined heating and/or power curves set for each individual cartridge. In certain embodiments, the controller is configured to independently and simultaneously control injection of a predetermined volume of vaporizable product into a plurality of cartridges on an individual cartridge basis according to a predetermined injection volume set for the individual cartridge. For example, the controller may be configured to operate linear actuators to dispense a predetermined volume from each of the containers (e.g. syringes), including on an individual basis.

Figure 31A:
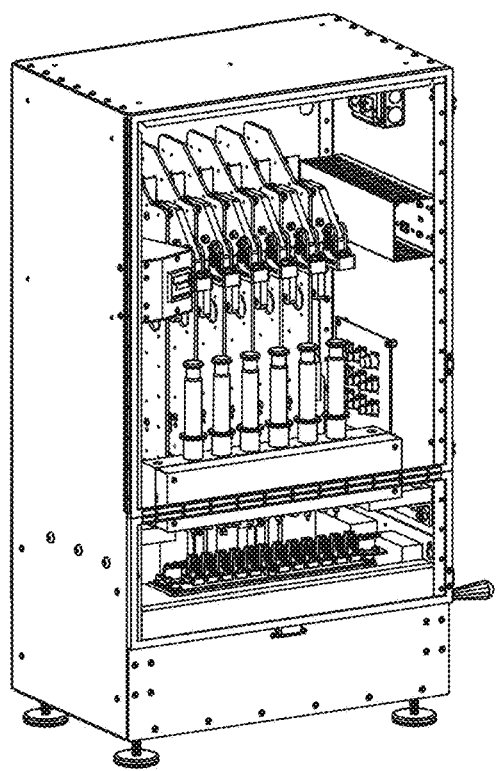
FIGS. 31A-31C are perspective views of the automated filling system according to aspects herein, showing different stages of the filling operation.
Figure 31B:
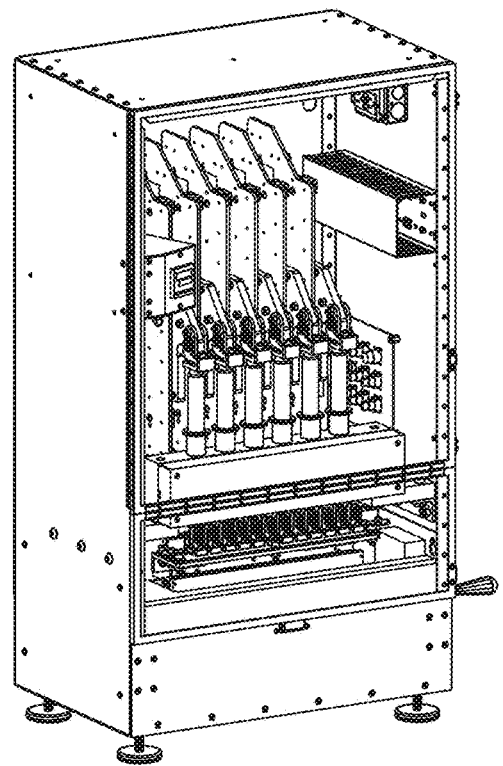
Figure 31C:
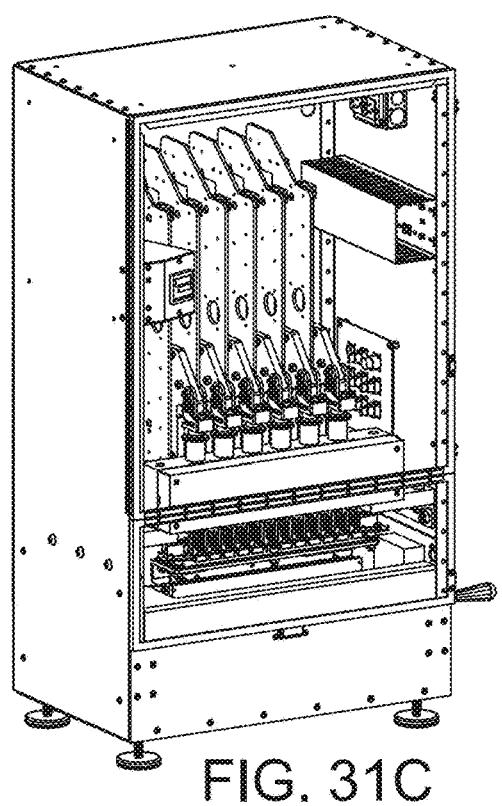
Figure 32:
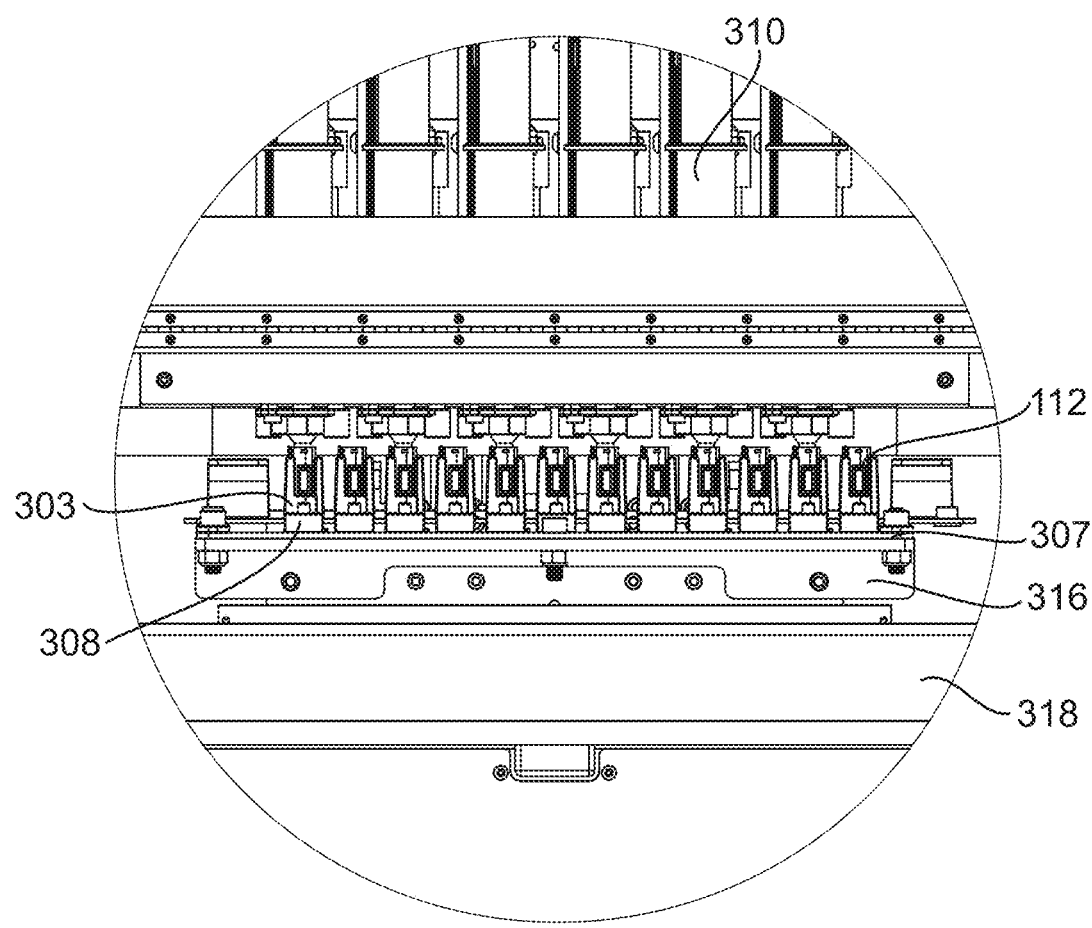
FIG. 32 is a front view of the filling tray of the automated filling system embodiment depicted in FIGS. 25A-25F.
Figure 33:
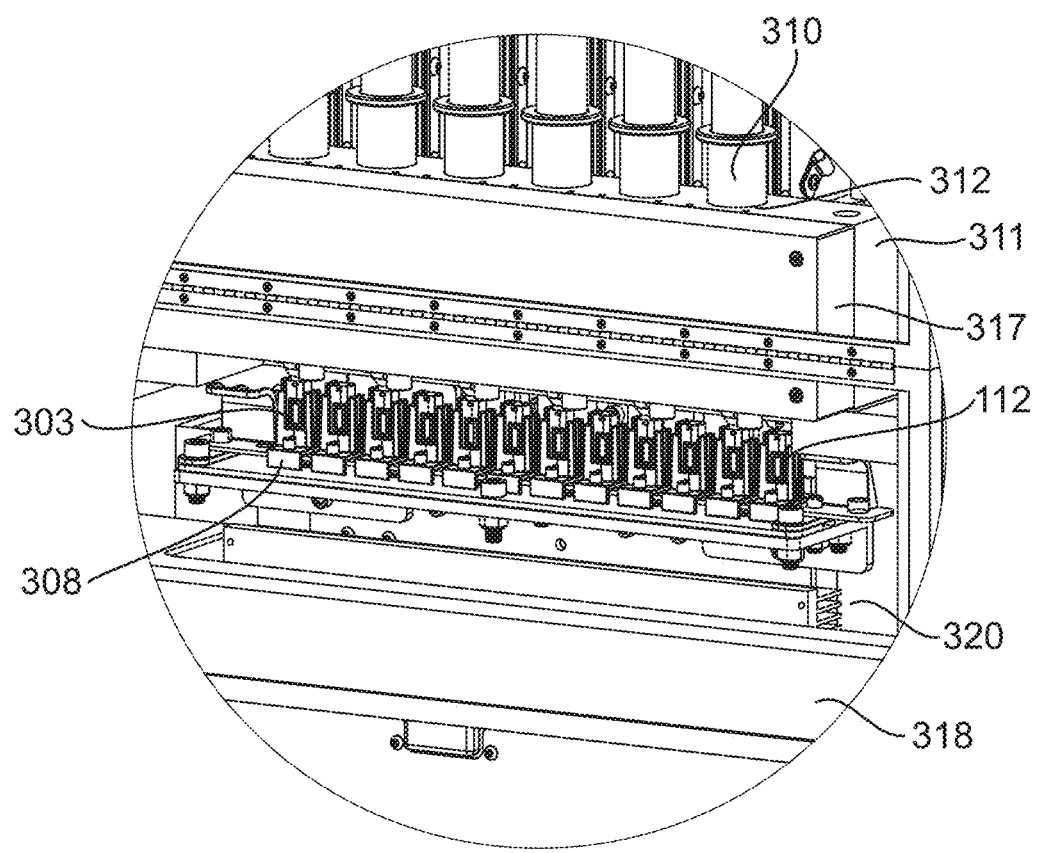
FIG. 33 is a perspective view of the filling tray of the automated filling system embodiment depicted in FIGS. 25A-25F.

During cartridge filling, according to certain embodiments several operations may take place (FIGS. 31A-31C). According to one embodiment, the vaporizable product in the syringe 310 may be pre-heated (e.g. to 115° C.) by the heat block 311, and the sliding shelf 316 with the filling tray 307 is moved up into position to place the cartridges in position with respect to the syringes, as shown in FIG. 31A. When the cartridges are in the correct position with respect to the syringes, the linear actuators 313 can push down on the syringe plunger 314, as shown in FIG. 31B, introducing the predetermined volume of vaporizable product into the vaporizable product receiving chamber 114 of the cartridge 112, such as for example as programmed by steps of the motor (now shown). To facilitate vaporizable product transfer down the vaporizable product receiving chamber, the internal heating element 136 in the cartridge is activated (e.g. before or after product injection) to further melt the vaporizable product over the duration of the filling. Power is supplied to the heating element 136 through the contact electrodes 306 embedded in the cartridge holder 303. In certain embodiments, the contact electrodes 306 are connected to individual PCBAs (printed circuit board assemblies) 315 that regulate temperature under a power curve specific to each vaporizable product (see FIG. 34). Referring to FIG. 28, in some embodiments, the PCBAs are located in a heat sink 320 below the sliding shelf 316/filling tray 307, and covered by an electrical shield 318. The PCBAs may form a portion of the controller of the automated system that controls the heating and injection systems of the automated system. The power going into the cartridge during filling is less than the operating power of the battery, so the temperature of the vaporizable product inside the cartridge will remain lower than when in a consumer battery operation, which may help to preserve the quality of the vaporizable product for use by the consumer. In some embodiments, the temperature of the porous valve element 126 is also elevated during the filling process, and the heat applied allows the vaporizable product to flow through and saturate the pores of the porous valve element. This combination of syringe and cartridge heating allows this system to fill cartridges at a fast rate, without excessively deteriorating the vaporizable product, and may even facilitates full saturation of the porous valve element, such as in a case where the porous valve element is itself heated at some point during the filling process. In certain embodiments, the automated filling process can be repeated by the system, e.g. tray by tray, until all contents within the syringes have been dispensed (FIG. 31C). Once the contents of the syringes have been completely dispensed, the linear actuators can be moved by the controller back to their original position, and any empty syringes can be replaced, such that the system is ready for filling of subsequent cartridges (FIG. 31A).

EMBODIMENTS

The Enumerated Embodiments 1-42 below set forth embodiments according to the disclosure.

Embodiment 1. A method for filling a cartridge used in a portable vaporizing device with a vaporizable product, wherein the cartridge comprises a vaporizable product receiving chamber configured to receive a vaporizable product therein and having upper and lower opposing ends, one or more internal heat-conducting surfaces within the vaporizable product receiving chamber and extending in between the upper and lower opposing ends thereof, and a porous valve element, the porous valve element being configured to at least partially vaporize the vaporizable product as it exits the vaporizable product receiving chamber by passing therethrough, the method comprising:

heating the one or more internal heat-conducting surfaces of the product receiving chamber;

introducing the vaporizable product into the upper end of the vaporizable product receiving chamber, such that the vaporizable product flows along the one or more heated internal heat-conducting surfaces of the product receiving chamber towards the lower end of the vaporizable product receiving chamber; and optionally, pre-heating the vaporizable product prior to introducing into the vaporizable product receiving chamber.

Embodiment 2. The method according Embodiment 1, wherein the cartridge comprises one or more chamber walls defining a product flow path between the upper and lower opposing ends of the vaporizable product receiving chamber, and wherein the one or more internal heat-conducting surfaces comprise at least one interior surface of the one or more chamber walls, the method comprising heating the at least one interior surface of the chamber walls, and introducing the vaporizable product into the upper end of the vaporizable product receiving chamber, such that the vaporizable product flows along the one or more heated interior surface(s) of the chamber walls toward the lower end of the vaporizable product receiving chamber.

Embodiment 3. The method according to any preceding Embodiment, wherein the cartridge comprises an elongate heat-conducting column within the vaporizable product receiving chamber and extending in between the upper and lower opposing ends therein, and wherein the one or more internal heat-conducting surfaces include at least one surface of the elongate heat-conducting column, and wherein the method comprising heating the elongate heat-conducting column, and introducing the vaporizable product into the upper end of the vaporizable product receiving chamber, such that the vaporizable product flows along the at least one heated surface of the elongate heat-conducting column toward the lower end of the vaporizable product receiving chamber.

Embodiment 4. The method according to any preceding Embodiment, wherein the one or more internal heat-conducting surfaces are heated by a heating element provided either separately or as a part of the cartridge.

Embodiment 5. The method according to any preceding Embodiment, wherein the one or more internal heat-conducting surfaces are heated by a heating element comprising one or more of a rod heater, a ring heater, a disc heater, a plate heater, a coil heater, and pancake coil.

Embodiment 6. The method according to any preceding Embodiment, wherein the elongate heat-conducting column is heated by contacting a base surface of the elongate heat-conducting column with a heating plate.

Embodiment 7. The method according to any preceding Embodiment, wherein the at least one interior surface of the chamber walls is heated by contacting outer surfaces of the chambers walls of the cartridge with a heating element.

Embodiment 8. The method according to any preceding Embodiment, wherein the one or more internal heat-conducting surfaces are pre-heated prior to introducing the vaporizable product into the vaporizable product receiving chamber.

Embodiment 9. The method according to any preceding Embodiment, wherein the one or more internal heat-conducting surfaces are heated simultaneously with, immediately prior to, or immediately after, initiation of injection of the vaporizable product into the vaporizable product receiving chamber.

Embodiment 10. The method according to any preceding Embodiment, wherein the one or more internal heat-conducting surfaces are pre-heated prior to initiation of injection of the vaporizable product into the vaporizable product receiving chamber, and wherein heating of the one or more internal heat-conducting surfaces is maintained during at least a portion of the duration of time in which the vaporizable product receiving chamber is filled with the vaporizable product.

Embodiment 11. The method according to any preceding Embodiment, wherein heating of the one or more internal heat-conducting surfaces is maintained during an entirety of a duration of time in which the vaporizable product receiving chamber is filled with the vaporizable product.

Embodiment 12. The method according to any preceding Embodiment, wherein the porous valve element is heated by a same or different heating element as the one or more internal heat-conducting surfaces, during at least a portion of a duration of time in which the vaporizable product receiving chamber is filled with the vaporizable product.

Embodiment 13. The method according to any preceding Embodiment, wherein the porous valve element is heated simultaneously with, immediately prior to, or immediately after, initiation of injection of the vaporizable product into the vaporizable product receiving chamber.

Embodiment 14. The method according to any preceding Embodiment, wherein the porous valve element is heated to at least partially saturate the porous valve element with the vaporizable product during filling of the vaporizable product receiving chamber.

Embodiment 15. The method according to any preceding Embodiment, wherein the one or more internal heat-conducting surfaces are heated to a temperature that is lower than an operational temperature of the one or more internal heat-conducting surfaces used for vaporization of the vaporizable product from the cartridge and inhalation thereof by a user.

Embodiment 16. The method according to any preceding Embodiment, wherein the one or more internal heat-conducting surfaces are heated to a temperature that is at least 20%, at least 25%, at least 30%, and/or at least 50% lower than the operational temperature of the one or more internal heat-conducting surfaces used for vaporization of the vaporizable product from the cartridge and inhalation thereof by the user.

Embodiment 17. The method according to any preceding Embodiment, wherein a wattage applied to a heating element to heat the one or more internal heat-conducting surfaces before, after, or simultaneously with, injection of the vaporizable product, is lower than an operational wattage of the one or more internal heat-conducting surfaces used for vaporization of the vaporizable product from the cartridge and inhalation thereof by a user.

Embodiment 18. The method according to any preceding Embodiment, wherein the wattage applied to the heating element to heat the one or more internal heat-conducting surfaces is at least 20%, at least 25%, at least 30%, and/or at least 50% lower than the operational wattage of the one or more internal heat-conducting surfaces used for vaporization of the vaporizable product from the cartridge and inhalation thereof by the user.

Embodiment 19. The method according to any preceding Embodiment, wherein a first wattage is applied to the heating element at the onset of heating of the one or more internal heat-conducting surfaces, and a second wattage that is lower than the first wattage is applied to the heating element while the vaporizable product fills up the vaporizable product receiving chamber.

Embodiment 20. The method according to any preceding Embodiment, wherein the vaporizable product is pre-heated to a temperature of at least 80° C., at least at least 100° C. and/or at least 110° C.

Embodiment 21. The method according to any preceding Embodiment, wherein the cartridge is supported during filling by a cartridge holder configured to hold the cartridge, the cartridge holder having contact electrodes configured to electrically contact the heating element to provide an electrical current for heating, and wherein a wattage supplied to the heating element by the contact electrodes heats the one or more internal heat-conducting surfaces.

Embodiment 22. The method according to any preceding Embodiment, wherein a wattage supplied to heat the one or more internal heat-conducting surfaces is regulated according to a predetermined power curve.

Embodiment 23. The method according to any preceding Embodiment, wherein the vaporizable product is injected from a container positioned over the upper end of the vaporizable product receiving chamber, and wherein the container is optionally heated by a heating block to pre-heat the vaporizable product.

Embodiment 24. The method according to any preceding Embodiment, wherein the vaporizable product is injected into the cartridge from a container corresponding to a syringe, and wherein a predetermined volume of vaporizable product is injected from the syringe into the cartridge by a linear actuator that pushes a syringe plunger into the syringe to dispense the predetermined volume therefrom.

Embodiment 25. The method according to any preceding Embodiment, comprising simultaneously filling a plurality of cartridges with vaporizable product, and wherein a power curve applied to heat the one or more internal heat-conducting surfaces in each of the plurality of cartridges is regulated individually for each cartridge.

Embodiment 26. An automated system for filling a cartridge used in a portable vaporizing device with a vaporizable product, wherein the cartridge comprises a vaporizable product receiving chamber configured to receive a vaporizable product therein and having upper and lower opposing ends, one or more internal heat-conducting surfaces within the vaporizable product receiving chamber and extending in between the upper and lower opposing ends thereof, and a porous valve element, the porous valve element being configured to at least partially vaporize the vaporizable product as it exits the vaporizable product receiving chamber by passing therethrough, the system comprising:
a housing;
a heating system configured to heat the one or more internal heat-conducting surfaces by supplying a power from a power source;
a holder within the housing configured to hold the cartridge;
an injection system within the housing configured to inject vaporizable product into the cartridge; and
a controller configured to control the heating system and injection system;
wherein the controller is configured to control the heating system to heat the one or more internal heat-conducting surfaces, and is configured to control the injection system to inject the vaporizable product into the upper end of the vaporizable product receiving chamber, such that the vaporizable product is at least partially melted and/or the viscosity of the vaporizable product is reduced as the vaporizable product flows along the heated one or more internal heat-conducting surfaces towards the lower end of the vaporizable product receiving chamber; and
optionally wherein the heating system is configured to pre-heat the vaporizable product in the injection system prior to introducing into the vaporizable product receiving chamber.

Embodiment 27. The automated system according to Embodiment 26, wherein the cartridge comprises one or more chamber walls defining a product flow path between the upper and lower opposing ends of the vaporizable product receiving chamber, and wherein the one or more internal heat-conducting surfaces comprise at least one interior surface of the one or more chamber walls, wherein the controller is configured to control the heating system to heat the at least one interior surface of the chamber walls, and is configured to control the injection system to inject the vaporizable product into the upper end of the vaporizable product receiving chamber, such that the vaporizable product flows along the one or more heated interior surface(s) of the chamber walls toward the lower end of the vaporizable product receiving chamber.

Embodiment 28. The automated system according to any preceding Embodiment, wherein the cartridge comprises an elongate heat-conducting column within the vaporizable product receiving chamber and extending in between the upper and lower opposing ends therein, and wherein the one or more internal heat-conducting surfaces include at least one surface of the elongate heat-conducting column, and wherein the controller is configured to control the heating system to heat the elongate heat-conducting column, and is configured to control the injection system to inject the vaporizable product into the upper end of the vaporizable product receiving chamber, such that the vaporizable product flows along the at least one heated surface of the elongate heat-conducting column toward the lower end of the vaporizable product receiving chamber.

Embodiment 29. The automated system according to any preceding Embodiment, wherein the heating system comprises a heating element provided either separately or as a part of the cartridge.

Embodiment 30. The automated system according to any preceding Embodiment, wherein the one or more internal heat-conducting surfaces are heated by a heating element comprising one or more of a rod heater, a ring heater, a disc heater, a plate heater, a coil heater, and pancake coil.

Embodiment 31. The automated system according to any preceding Embodiment, wherein the elongate heat-conducting column is heated by contacting a base surface of the elongate heat-conducting column with a heating plate.

Embodiment 32. The automated system according to any preceding Embodiment, wherein the at least one interior surface of the chamber walls is heated by contacting outer surfaces of the chambers walls of the cartridge with a heating element.

Embodiment 33. The automated system according to any preceding Embodiment, wherein the controller is configured to control the heating system to heat the one or more internal heat-conducting surfaces before, after, and/or simultaneously with controlling the injection system to inject the vaporizable product into the vaporizable product receiving chamber of the cartridge.

Embodiment 34. The automated system according to any preceding Embodiment, wherein the cartridge holder comprises contact electrodes configured to electrically contact the heating element to provide an electrical current from the power source for heating, and wherein a wattage supplied to the heating element by the contact electrodes from the power source heats the one or more internal heat-conducting surfaces.

Embodiment 35. The automated system according to any preceding Embodiment, wherein the cartridge holder comprises a filling tray comprising a plurality of wells configured to hold a plurality of cartridges, and wherein the plurality of wells comprise contact electrodes located at a bottom of each well.

Embodiment 36. The automated system according to any preceding Embodiment, wherein the injection system comprises an injection container support configured to support a plurality of containers with vaporizable product therein at a position above or inside the upper ends of a plurality of vaporizable product receiving chambers.

Embodiment 37. The automated system according to any preceding Embodiment, wherein the injection system comprises a heat block having a plurality of holes therethrough to fit a plurality of containers containing the vaporizable product, and wherein the heat block is heated by the heating system to heat the vaporizable product held in the plurality of containers.

Embodiment 38. The automated system according to any preceding Embodiment, wherein the injection system comprises a plurality of containers corresponding to a plurality of syringes to hold the vaporizable product for injection into the cartridges.

Embodiment 39. The automated system according to any preceding Embodiment, wherein the injection system comprises a plurality of linear actuators located above the containers, which are configured to move down to physically contact ends of plungers that engage a top end of the containers to push the vaporizable product through the containers and dispense into the cartridges, the linear actuators being operably connected to the power source.

Embodiment 40. The automated system according to any preceding Embodiment, wherein the controller is configured to independently and simultaneously control heating of a plurality of cartridges on an individual cartridge basis according to predetermined heating and/or power curves set for each individual cartridge.

Embodiment 41. The automated system according to any preceding Embodiment, wherein the controller is configured to independently and simultaneously control injection of a predetermined volume of vaporizable product into a plurality of cartridges on an individual cartridge basis according to a predetermined injection volume set for the individual cartridge.

Embodiment 42. A method of automated filling of a cartridge using the automated system according to any preceding Embodiment, the method comprising:
(a) filling one or more syringes with vaporizable product;
(b) placing one or more empty cartridges in a cartridge holder;
(c) determining the target volume to fill in the cartridge based on the size of the cartridge, and entering the target volume into a pre-programed motor;
(d) heating the syringes and cartridges to respective predetermined temperatures;
(e) after (d), performing a filling process by pushing down syringe plungers to dispense product from the syringe into the clips; and
(f) resetting the system by moving up the linear actuators and replacing the empty syringes.

EQUIVALENTS

While specific embodiments have been discussed, the above specification is illustrative, and not restrictive. Many variations will become apparent to those skilled in the art upon review of this specification. The full scope of the embodiments should be determined by reference to the claims, along with their full scope of equivalents, and the specification, along with such variations.

What is claimed is:

1. A method for filling a cartridge used in a portable vaporizing device with a vaporizable product, wherein the cartridge comprises a vaporizable product receiving chamber configured to receive a vaporizable product therein and having upper and lower opposing ends, one or more internal heat-conducting surfaces within the vaporizable product receiving chamber and extending in between the upper and lower opposing ends thereof, and a porous valve element, the porous valve element being configured to at least partially vaporize the vaporizable product as it exits the vaporizable product receiving chamber by passing therethrough, the method comprising:
heating the one or more internal heat-conducting surfaces of the vaporizable product receiving chamber;
introducing the vaporizable product into the upper opposing end of the vaporizable product receiving chamber, such that the vaporizable product flows along the one or more heated internal heat-conducting surfaces of the vaporizable product receiving chamber towards the lower opposing end of the vaporizable product receiving chamber; and
optionally, pre-heating the vaporizable product prior to introducing into the vaporizable product receiving chamber.

2. The method according to claim 1, wherein the cartridge comprises one or more chamber walls defining a product flow path between the upper and lower opposing ends of the vaporizable product receiving chamber, and wherein the one or more internal heat-conducting surfaces comprise at least one interior surface of the one or more chamber walls, the method comprising heating the at least one interior surface of the one or more chamber walls, and introducing the vaporizable product into the upper opposing end of the vaporizable product receiving chamber, such that the vaporizable product flows along the one or more heated interior surface(s) of the one or more chamber walls toward the lower opposing end of the vaporizable product receiving chamber.

3. The method according to claim 1, wherein the cartridge comprises an elongate heat-conducting column within the vaporizable product receiving chamber and extending in between the upper and lower opposing ends therein, and wherein the one or more internal heat-conducting surfaces include at least one surface of the elongate heat-conducting column, and wherein the method comprising heating the elongate heat-conducting column, and introducing the vaporizable product into the upper opposing end of the vaporizable product receiving chamber, such that the vaporizable product flows along the at least one heated surface of the elongate heat-conducting column toward the lower opposing end of the vaporizable product receiving chamber.

4. The method according to any preceding claim, wherein the one or more internal heat-conducting surfaces are heated by a heating element provided either separately or as a part of the cartridge.

5. The method according to claim 3, wherein the elongate heat-conducting column is heated by contacting a base surface of the elongate heat-conducting column with a heating plate.

6. The method according to claim 2, wherein the at least one interior surface of the one or more chamber walls is heated by contacting outer surfaces of the one or more chambers walls of the cartridge with a heating element.

7. An automated system for filling a cartridge used in a portable vaporizing device with a vaporizable product, wherein the cartridge comprises a vaporizable product receiving chamber configured to receive a vaporizable product therein and having upper and lower opposing ends, one or more internal heat-conducting surfaces within the vaporizable product receiving chamber and extending in between the upper and lower opposing ends thereof, and a porous valve element, the porous valve element being configured to at least partially vaporize the vaporizable product as it exits the vaporizable product receiving chamber by passing therethrough, the system comprising:
a housing;
a heating system configured to heat the one or more internal heat-conducting surfaces by supplying a power from a power source;
a holder within the housing configured to hold the cartridge;
an injection system within the housing configured to inject the vaporizable product into the cartridge; and a controller configured to control the heating system and injection system; wherein the controller is configured to control the heating system to heat the one or more internal heat-conducting surfaces, and is configured to control the injection system to inject the vaporizable product into the upper opposing end of the vaporizable product receiving chamber, such that the vaporizable product is at least partially melted and/or the viscosity of the vaporizable product is reduced as the vaporizable product flows along the heated one or more internal heat-conducting surfaces towards the lower opposing end of the vaporizable product receiving chamber; and optionally wherein the heating system is configured to pre-heat the vaporizable product in the injection system prior to introducing into the vaporizable product receiving chamber.

8. The automated system according to claim 7, wherein the cartridge comprises one or more chamber walls defining a product flow path between the upper and lower opposing ends of the vaporizable product receiving chamber, and wherein the one or more internal heat-conducting surfaces comprise at least one interior surface of the one or more chamber walls, wherein the controller is configured to control the heating system to heat the at least one interior surface of the one or more chamber walls, and is configured to control the injection system to inject the vaporizable product into the upper opposing end of the vaporizable product receiving chamber, such that the vaporizable product flows along the one or more heated interior surface(s) of the one or more chamber walls toward the lower opposing end of the vaporizable product receiving chamber.

9. The automated system according to claim 7, wherein the cartridge comprises an elongate heat-conducting column within the vaporizable product receiving chamber and extending in between the upper and lower opposing ends therein, and wherein the one or more internal heat-conducting surfaces include at least one surface of the elongate heat-conducting column, and wherein the controller is configured to control the heating system to heat the elongate heat-conducting column, and is configured to control the injection system to inject the vaporizable product into the upper opposing end of the vaporizable product receiving chamber, such that the vaporizable product flows along the at least one heated surface of the elongate heat-conducting column toward the opposing lower end of the vaporizable product receiving chamber.

10. The automated system according to any one of claims 7-9, wherein the heating system comprises a heating element provided either separately or as a part of the cartridge.

11. The automated system according to claim 9, wherein the elongate heat-conducting column is heated by contacting a base surface of the elongate heat-conducting column with a heating plate.

12. The automated system according to claim 8, wherein the at least one interior surface of the one or more chamber walls is heated by contacting outer surfaces of the one or more chambers walls of the cartridge with a heating element.

* * * * *